United States Patent
Fuh et al.

[11] Patent Number: 5,945,412
[45] Date of Patent: Aug. 31, 1999

[54] METHODS AND COMPOSITIONS FOR PREVENTING AND TREATING BONE LOSS

[75] Inventors: Vivian L. Fuh, New York, N.Y.; Keith D. Kaufman, Westfield; Joanne Waldstreicher, Scotch Plains, both of N.J.

[73] Assignee: Merck & Co., Inc., Rahway, N.J.

[21] Appl. No.: 08/984,425

[22] Filed: Dec. 3, 1997

Related U.S. Application Data

[60] Provisional application No. 60/032,634, Dec. 9, 1996.

[51] Int. Cl.$^6$ .......................... A61K 31/58; A61K 31/56; A61K 31/44
[52] U.S. Cl. .......................... 514/176; 514/171; 514/284
[58] Field of Search ...................................... 514/167, 176, 514/298, 324, 284, 171

[56] References Cited

U.S. PATENT DOCUMENTS

| | | | |
|---|---|---|---|
| 5,512,555 | 4/1996 | Waldstreicher | 514/168 |
| 5,543,417 | 8/1996 | Waldstreicher | 514/284 |
| 5,550,134 | 8/1996 | Audia et al. | 514/284 |
| 5,670,514 | 9/1997 | Audia et al. | 514/298 |

FOREIGN PATENT DOCUMENTS

WO 95/11254  4/1995  WIPO.

OTHER PUBLICATIONS

Durette et al., Database Caplus on STN, 1995.
Durette et al., Database Caplus on STN, 1993.
Rosen et al., Endocrinology 136 (1995), pp. 1381–1387, "Bone density is normal in male rats treated with finasteride."
Tollin et al., J. Clin. Endoc. Metab. 81 (1996), pp. 1031–1034, "Finasteride therapy does not alter bone turnover in men with benign prostatic hyperplasia. . . ".
Matzkin et al., Clin. Endocrinol. 37 (1992), pp. 432–436, "Prolonged treatment with finasteride (a 5alpha–reductase inhibitor) does not affect bone density and metabolism."

*Primary Examiner*—Theodore J. Criares
*Attorney, Agent, or Firm*—Catherine D. Fitch; Melvin Winokur

[57] ABSTRACT

The present invention provides for a method of inhibiting bone loss in a subject in need of such treatment comprising administration to the subject of a therapeutically effective amount of a compound of structural formula I:

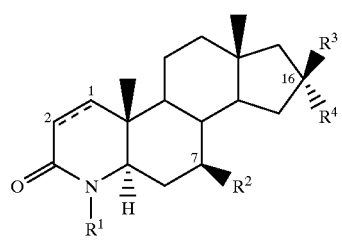

The present invention further provides for a method for treating and preventing osteoporosis and osteopenia and other diseases where inhibiting bone loss may be beneficial, including: Paget's disease, malignant hypercalcemia, periodontal disease, joint loosening and metastatic bone disease, comprising administration of therapeutically effective amount of a compound of structural formula I to the subject.

Further, the present invention provides for compositions useful in the methods of the present invention, as well as a method of manufacture of a medicament useful for inhibiting bone loss and treating or preventing osteoporosis and osteopenia.

29 Claims, No Drawings

METHODS AND COMPOSITIONS FOR PREVENTING AND TREATING BONE LOSS

CROSS-REFERENCE TO RELATED APPLICATIONS

The present application claims priority to U.S. Provisional Patent Application Ser. No. 60/032,634, filed Dec. 9, 1996, now abandoned.

FIELD OF THE INVENTION

The present invention provides for a novel method of preventing and/or treating bone loss. Further, the present invention is directed to methods of treating and/or preventing osteoporosis and osteopenia and other diseases where inhibiting bone loss may be beneficial, including: Paget's disease, malignant hypercalcemia, periodontal disease, joint loosening and metastatic bone disease, as well as reducing the risk of fractures, both vertebral and nonvertebral. The present invention also provides for a method of manufacture of a medicament useful for inhibiting bone loss, and for preventing and/or treating osteoporosis and osteopenia and other diseases where inhibiting bone loss may be beneficial, including: Paget's disease, malignant hypercalcemia, periodontal disease, joint loosening and metastatic bone disease, as well as reducing the risk of fractures, both vertebral and nonvertebral. The present invention also provides for compositions useful in the methods of inhibiting bone loss and treating and/or preventing osteoporosis and osteopenia and other diseases where inhibiting bone loss may be beneficial, including: Paget's disease, malignant hypercalcemia, periodontal disease, joint loosening and metastatic bone disease, as well as reducing the risk of fractures, both vertebral and nonvertebral.

BACKGROUND OF THE INVENTION

The mechanism of bone loss is not well understood, but in practical effect, the disorder arises from an imbalance in the formation of new healthy bone and the resorption of old bone, with the result being a net loss of bone tissue. This bone loss includes a decrease in both mineral content and protein matrix components of the bone, and leads to an increased fracture rate of, predominantly, femoral bones and bones in the forearm and vertebrae. These fractures, in turn, lead to an increase in general morbidity, a marked loss of stature and mobility, and, in many cases, an increase in mortality resulting from complications.

Bone loss occurs in a wide range of subjects including aging men and women, post-menopausal women, patients who have undergone hysterectomy, patients who are undergoing or have undergone long-term administration of corticosteroids, patients suffering from Cushing's syndrome, and patents having gonadal dysgenesis.

Unchecked, bone loss can lead to osteoporosis and/or osteopenia. Osteopenia is reduced bone mass due to a decrease in the rate of osteoid synthesis to a level insufficient to compensate normal bone lysis. Osteoporosis is a major debilitating disease whose prominent feature is the loss of bone mass (decreased density and enlargement of bone spaces) without a reduction in bone volume, producing porosity and fragility.

One on the most common types of osteoporosis is found in post-menopausal women affecting an estimated 20 to 25 million women in the United States alone. A significant feature of post-menopausal osteoporosis is the large and rapid loss of bone mass due to the cessation of estrogen production by the ovaries. Indeed, estrogens have been shown to limit the progression of osteoporotic bone loss, and estrogen replacement is a recognized treatment for post-menopausal osteoporosis in the United States and many other countries. Although the administration of estrogens have beneficial effects on bone when given even at very low levels, long-term estrogen therapy has been implicated in a variety of disorders such as an increase in the risk of uterine and breast cancer, vaginal bleeding, and endometrial hyperplasia, causing many women to avoid this treatment. Recently suggested therapeutic regimens which seek to lessen the cancer risk, such as administering combinations of progestogen and estrogen, may be linked to negative cardiovascular effects. Concerns over the significant undesirable effects associated with estrogen therapy, and the limited ability of estrogens to reverse existing bone loss, support the need to develop alternative therapy for bone loss that generates the desirable effects on bone but does not cause undesirable effects.

Attempts to fill this need by the use of compounds commonly known as antiestrogens, which interact with the estrogen receptor, have had limited success, perhaps due to the fact that these compounds generally display a mixed agonist/antagonist effect. That is, although these compounds can antagonize estrogen interaction with the receptor, the compounds themselves may cause estrogenic responses in those tissues having estrogen receptors. Therefore, some antiestrogens, when administered alone, are subject to the same adverse effects associated with estrogen therapy.

Osteoporosis and osteopenia are present in both aging men and women, due to age-related bone loss.

Other treatments used for osteoporosis include vitamin and mineral supplementation with calcium and vitamin D. This has limited effectiveness in treating advanced disease and regular disease. The effectiveness of this treatment is limited in treating and preventing bone loss.

Treatment with bisphosphonates such as alendronate, currently marketed by Merck & Co., Inc. as FOSAMAX®, has also been successfuil in inhibiting bone loss and increasing bone density. Bisphosphonates have low bioavailability and their administration must avoid food interactions. Treatment with shots or intranasal Calcitonin and low dose PTH (parathyroid horomone) shots have also been employed in an effort to inhibit bone loss and treat or prevent osteoporosis. Treatment with calcitonin is associated with a high rate of allergic reaction.

Treatments used for bone loss in men include vitamin and mineral supplementation with calcium and vitamin D. This has limited effectiveness in treating advanced disease and regular disease. The effectiveness of this treatment is limited in treating and preventing bone loss.

Also, bone loss in men is treated with androgens such as testosterone. Treatment with testosterone can lead to baldness, acne, lowering of HDL cholesterol (the "good" cholesterol) and raising of LDL cholesteroal (the "bad" cholesterol), and it may be associated with an increased risk of prostate cancer and benign prostatic hyperplasia.

U.S. Pat. No. 5,550,134, issued Aug. 27, 1996, describes methods for inhibiting the loss of bone with benzoquinolin-3-ones known to be inhibitors of the enzyme 5α-reductase type 1.

The present invention relates to methods of inhibiting bone loss without the associated adverse effects of hormone replacement therapy, and thus, serves as an effective acceptable treatment for osteoporosis and osteopenia and other diseases where inhibiting bone loss may be beneficial, including: Paget's disease, malignant hypercalcemia, periodontal disease, joint loosening and metastatic bone disease, as well as reducing the risk of fractures, both vertebral and nonvertebral. It has now been found that a 5α-reductase type 1 inhibitors of structural formula I:

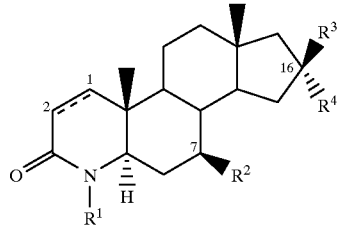

I are useful for the inhibition of bone loss and the treatment of the associated clinical conditions. In particular, the present invention relates to the use of compounds of structural formula I for the inhibition of bone loss and the treatment and prevention of osteoporosis and osteopenia and other diseases where inhibiting bone loss may be beneficial, including: Paget's disease, malignant hypercalcemia, periodontal disease, joint loosening and metastatic bone disease, as well as reducing the risk of fractures, both vertebral and nonvertebral. The inhibition of bone loss contemplated by the present methods includes both medical therapeutic and/or prophylactic treatment, as appropriate.

The enzyme 5α-reductase catalyzes the reduction of testosterone (T) to the more potent androgen, 5α-dihydrotestosterone (dihydrotestosterone" or DHT), as shown below:

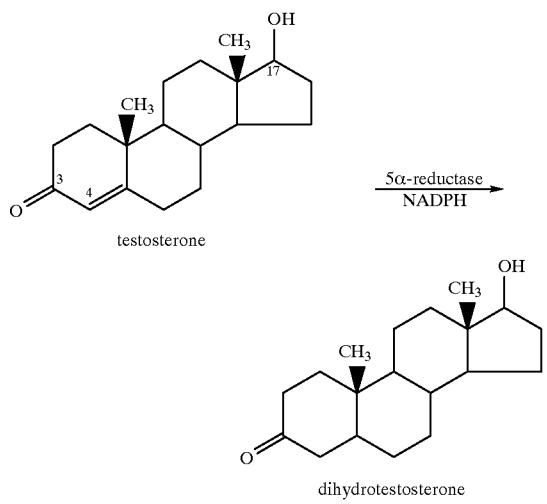

There are two isozymes of 5α-reductase in humans. Andersson, et al., Proc. Natl. Acad. Sci. USA, 87:3640–44 (1990); Andersson, et al., Nature, 354, 159–61 (1991). The isozymes, usually called Type 1 and Type 2, exhibit differences in their biochemical properties, genetics, and pharmacology. Both isozymes are now the subject of considerable research and it has been found one isozyme (type 1) predominates in he sebaceous glands of facial skin and skin tissue and that the other (type 2) predominates in the prostate.

Finasteride (17β-(N-tert-butylcarbamoyl)-3-oxo-4-aza-5α-androst-1-en-3-one) as shown below, is a potent inhibitor of the human type 2 enzyme.

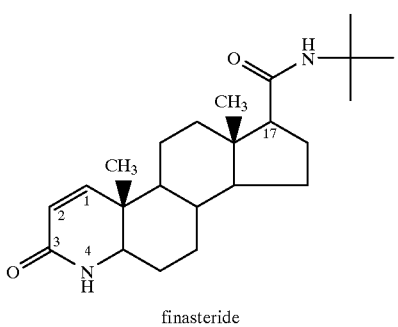

finasteride

Under the tradename PROSCAR®, finasteride is known to be useful in the treatment of hyperandrogenic conditions, see e.g., U.S. Pat. No. 4,760,071. Finasteride is currently prescribed for the treatment of benign prostatic hyperplasia (BPH), a condition affecting to some degree the majority of men over age 55. Finasteride's usefulness in the treatment of androgenic alopecia and prostatic cancer is described in the following documents: EP 0 285 382, published Oct. 5, 1988, EP 0 285 383, published Oct. 5, 1988 and Canadian patents 1,302,277 and 1,302,276.

SUMMARY OF THE INVENTION

The present invention provides for a method of inhibiting bone loss in a subject in need of such treatment comprising administration of a therapeutically effective amount of a compound of structural formula I:

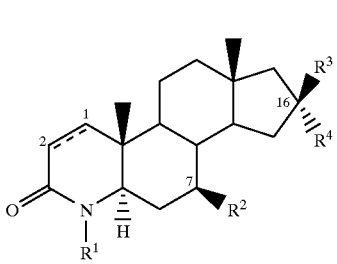

I to the subject. The present invention further provides for a method for treating and preventing osteoporosis and osteopenia and other diseases where inhibiting bone loss may be beneficial, including: Paget's disease, malignant hypercalcemia, periodontal disease, joint loosening and metastatic bone disease as well as reducing the risk of fractures, both vertebral and nonvertebral, comprising administration of therapeutically effective amount of compound of structural formula I to the subject. Further, the present invention provides for compositions useful in the methods of the present invention, as well as a method of manufacture of a medicament useful for inhibiting bone loss and treating or preventing osteoporosis and osteopenia.

DETAILED DESCRIPTION OF THE INVENTION

In one embodiment, the present invention is directed to a method for inhibiting bone loss in a subject in need thereof by administering to the subject an effective amount of a compound of structural formula I:

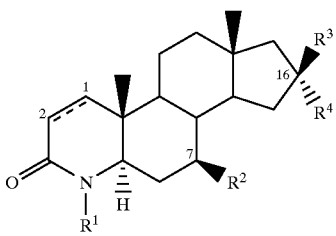

or a pharmaceutically acceptable salt or ester thereof wherein:

the C1—C2 carbon-carbon bond may be a single bond, or a double bond as indicated by the dashed line;

$R^1$ is selected from the group consisting of hydrogen and $C_{1-10}$ alkyl;

$R^2$ is selected from the group consisting of hydrogen and $C_{1-10}$ alkyl;

one of $R^3$ and $R^4$ is selected from the group consisting of hydrogen and methyl, and the other is selected from the group consisting of:
(a) amino;
(b) cyano;
(c) fluoro;
(d) methyl;
(e) OH;
(f) —C(O)NR$_b$R$_c$, where R$_b$ and R$_c$ are independently H, $C_{1-6}$ alkyl, aryl, or aryl$C_{1-6}$alkyl; wherein the alkyl moiety can be substituted with 1–3 of: halo; $C_{1-4}$alkoxy; or trifluoromethyl; and the aryl moiety can be substituted with 1–3 of: halo; $C_{1-4}$alkyl; $C_{1-4}$ alkoxy; or trifluoromethyl;
(g) $C_{1-10}$ alkyl—X—;
(h) $C_{2-10}$ alkenyl—X—;
wherein the $C_{1-10}$ alkyl in (g) and $C_{2-10}$ alkenyl in (h) can be unsubstituted or substituted with one to three of:
i) halo; hydroxy; cyano; nitro; mono-, di- or trihalomethyl; oxo; hydroxysulfonyl; carboxy;
ii) hydroxy$C_{1-6}$alkyl; $C_{1-6}$alkyloxy; $C_{1-6}$ alkylthio; $C_{1-6}$alkylsulfonyl; $C_{1-6}$ alkyloxycarbonyl; in which the $C_{1-6}$ alkyl moiety can be further substituted with 1–3 of: halo; $C_{1-4}$ alkoxy; or trifluoromethyl;
iii) arylthio; aryl; aryloxy; arylsulfonyl; aryloxycarbonyl; in which the aryl moiety can be further substituted with 1–3 of: halo; $C_{1-4}$ alkyl; $C_{1-4}$ alkoxy; or trifluoromethyl;
iv) —C(O )NR$_b$R$_c$; —N(Rb)—C(O)—R$_c$; —NR$_b$R$_c$; where R$_b$ and R$_c$ are defined above;
(i) aryl—X—;
(j) heteroaryl—X—, wherein heteroaryl is a 5, 6 or 7 membered heteroaromatic ring containing at least one member selected from the group consisting of: one ring oxygen atom, one ring sulfur atom, 1–4 ring nitrogen atoms, or combinations thereof; in which the heteroaromatic ring can also be fused with one benzo or heteroaromatic ring; wherein the aryl in (i) and heteroaryl in (j) can be unsubstituted or substituted with one to three of:
v) halo; hydroxy; cyano; nitro; mono-, di- or trihalomethyl; mono-, di- or trihalomethoxy; $C_{2-6}$ alkenyl; $C_{3-6}$ cycloalkyl; formyl; hydrosulfonyl; carboxy; ureido;
vi) $C_{1-6}$ alkyl; hydroxy $C_{1-6}$ alkyl; $C_{1-6}$ alkyloxy; $C_{1-6}$ alkyloxy $C_{1-6}$alkyl; $C_{1-6}$ alkylcarbonyl; $C_{1-6}$ alkylsulfonyl; $C_{1-6}$ alkylthio; $C_{1-6}$ alkylsulfinyl; $C_{1-6}$ alkylsulfonamido; $C_{1-6}$ alkylarylsulfonamido; $C_{1-6}$ alkyloxy-carbonyl; $C_{1-6}$ alkyloxycarbonyl $C_{1-6}$alkyl; R$_b$R$_c$N—C(O)—$C_{1-6}$alkyl; $C_{1-6}$ alkanoylamino $C_{1-6}$ alkyl; aroylamino $C_{1-6}$ alkyl; wherein the $C_{1-6}$ alkyl moiety can be substituted with 1–3 of: halo; $C_{1-4}$alkoxy; or trifluoromethyl;
vii) aryl; aryloxy; arylcarbonyl; arylthio; arylsulfonyl; arylsulfinyl; arylsulfonamido; aryloxycarbonyl; wherein the aryl moiety can be substituted with 1–3 of: halo; $C_{1-4}$alkyl; $C_{1-4}$alkoxy; or trifluoromethyl;
viii) —C(O)NR$_b$R$_c$; —O—C(O)—NR$_b$R$_c$; —N(R$_b$)—C(O)—R$_c$; —NR$_b$R$_c$; R$_b$—C(O)—N (R$_c$)—; where R$_b$ and R$_c$ are defined in (f) above; and —N(R$_b$)—C(O)—OR$_g$, wherein R$_g$ is $C_{1-6}$alkyl or aryl, in which the alkyl moiety can be substituted with 1–3 of: halo; $C_{1-4}$alkoxy; or trifluoromethyl, and the aryl moiety can be substituted with 1–3 of: halo; $C_{1-4}$alkyl; $C_{1-4}$ alkoxy, or trifluoromethyl; —N(Rb)—C(O) NR$_c$R$_d$, wherein R$_d$ is selected from H, $C_{1-6}$ alkyl, and aryl; in which said $C_{1-6}$alkyl and aryl can be substituted as described above in (f) for R$_b$ and R$_c$;
ix) a heterocyclic group, which is a 5, 6 or 7 membered ring, containing at least one member selected from the group consisting of: one ring oxygen atom, one ring sulfur atom, 1–4 ring nitrogen atoms, or combinations thereof; in which the heterocyclic ring can be aromatic, unsaturated, or saturated, wherein the heterocyclic ring can be fused with a benzo ring, and
wherein said heterocyclic ring can be substituted with one to three substituents, as defined above for v), vi), vii) and viii), excluding ix) a heterocyclic group; and
(k) $R^3$ and $R^4$ taken together can be carbonyl oxygen;
(l) $R^3$ and $R^4$ taken together can be =CH—R$_g$, wherein R$_g$ is defined in viii); and wherein:
X is selected from the group consisting of:
—O—; —S(O)$_n$—; —C(O)—; —CH(R$_e$)—; —C(O)—O—*; —C(O)—N(Re)—*; —N(R$_e$)—C(O)—O—*; —O—C(O)—N(R$_e$)—*; —N(R$_e$)C(O)—N(R$_e$)—; —O—CH(R$_e$)—*; —N(R$_e$)—*; wherein R$_e$ is H, $C_{1-3}$ alkyl, aryl, aryl—$C_{1-3}$ alkyl, or unsubstituted or substituted heteroaryl, as defined above in (j);
wherein the asterisk (*) denotes the bond which is attached to the 16-position in Structure I; and n is zero, 1 or 2.

Still a further aspect of the present invention is a method of preventing diseases of the bone where inhibiting bone loss may be beneficial, including: osteoporosis, osteopenia, Paget's disease, malignant hypercalcemia, periodontal disease, joint loosening and metastatic bone disease, as well as reducing the risk of fractures, both vertebral and nonvertebral, in a subject in need thereof by administering an effective amount of a compound of structural formula I to the subject.

Still another aspect of the present invention is the method of reducing the risk of diseases of the bone where inhibiting bone loss may be beneficial, including: osteoporosis, osteopenia, Paget's disease, malignant hypercalcemia, periodontal disease, joint loosening and metastatic bone disease, as well as reducing the risk of fractures, both vertebral and nonvertebral, in a subject at risk therefor by administering an effective amount of a compound of structural formula I to a subject.

Yet a further aspect of the present invention is the method of treating diseases of the bone where inhibiting bone loss may be beneficial, including: osteoporosis, osteopenia, Paget's disease, malignant hypercalcemia, periodontal disease, joint loosening and metastatic bone disease, as well as reducing the risk of fractures, both vertebral and nonvertebral, in a subject in need thereof by administration of an effective amount of a compound of structural formula I to the subject.

Another aspect of the present invention is the use of a compound of structural formula I for the manufacture of a medicament useful to inhibit bone loss in a subject in need thereof. Still a further aspect of the present invention is the use of a compound of structural formula I for the manufacture of a medicament useful to prevent diseases of the bone where inhibiting bone loss may be beneficial, including: osteoporosis, osteopenia, Paget's disease, malignant hypercalcemia, periodontal disease, joint loosening and metastatic bone disease, as well as reducing the risk of fractures, both vertebral and nonvertebral. Still another aspect of the present invention is the use of a compound of structural formula I for the manufacture of a medicament useful to reduce the risk of diseases of the bone where inhibiting bone loss may be beneficial, including: osteoporosis, osteopenia, Paget's disease, malignant hypercalcemia, periodontal disease, joint loosening and metastatic bone disease, as well as reducing the risk of fractures, both vertebral and nonvertebral, in a subject at risk therefor. Yet a further aspect of the present invention is the use of a compound of structural formula I for the manufacture of a medicament useful to treat diseases of the bone where inhibiting bone loss may be beneficial, including: osteoporosis, osteopenia, Paget's disease, malignant hypercalcemia, periodontal disease, joint loosening and metastatic bone disease, as well as reducing the risk of fractures, both vertebral and nonvertebral.

In one embodiment of the present invention compounds of structural Formula I wherein $R^1$ is hydrogen or methyl and $R^2$ is hydrogen or methyl are employed.

A further embodiment of the present invention employs compounds of Formula I wherein:

one of $R^3$ and $R^4$ is selected from the group consisting of hydrogen and methyl, and the other is selected from the group consisting of:
(b) cyano;
(c) fluoro;
(e) OH;
(g) $C_{1-10}$ alkyl—X—; or $C_{1-10}$ alkyl—X—, where alkyl can be substituted with aryl, and wherein aryl in turn can be substituted with 1-2 of halo or $C_{1-6}$alkyl;
(h) $C_{2-10}$ alkenyl—X—;
(i) aryl—X—;
(j) heteroaryl—X—, wherein heteroaryl is a 5 or 6 membered heteroaromatic ring containing 1-2 ring nitrogen atoms; wherein the aryl in (i) and heteroaryl in (j) can be unsubstituted or substituted with one to two of:
x) halo; cyano; nitro; trihalomethyl; trihalomethoxy; $C_{1-6}$ alkyl; aryl; $C_{1-6}$ alkylsulfonyl; $C_{1-6}$ alkylarylsulfonamino;
xi) —$NR_bR_c$; $R_b$—C(O)—N($R_c$)—; wherein $R_b$ and $R_c$ are independently H, $C_{1-6}$ alkyl, aryl, or aryl$C_{1-6}$alkyl; wherein the alkyl moiety can be substituted with 1–3 of: halo; $C_{1-4}$alkoxy; or trifluoromethyl;

and the aryl moiety can be substituted with 1–3 of: halo; $C_{1-4}$alkyl; $C_{1-4}$ alkoxy; or trifluoromethyl;
xii) a heterocyclic group, which is a 5 membered aromatic ring, containing one ring nitrogen atom, or one ring oxygen and one ring nitrogen atom; and (k) wherein $R^3$ and $R^4$ taken together can be carbonyl oxygen; and wherein:

X is selected from the group consisting of:
—O—; —S(O)$_n$—; —CH($R_e$)—; —C(O)—N($R_e$)—*; —O—C(O)—N($R_e$)—*;
wherein $R_e$ is H, $C_{1-3}$ alkyl, aryl, aryl $C_{1-3}$ alkyl;
wherein the asterisk (*) denotes the bond which is attached to the 16-position in Structure I; and n is zero or 2.

Compounds of Formula I which may be employed in the present invention include but are not limited to the following:
4-aza-4,7,β-dimethyl-5α-androstane-3, 16-dione;
4-aza-4-methyl-5α-androstan-3, 16-dione;
3-oxo-4-aza-4-methyl-16β-hydroxy-5α-androstane;
3-oxo-4-aza-4-methyl-16β-(benzylaminocarbonyloxy)-5α-androstane;
3-oxo-4-aza-4-methyl-16β-benzoylamino-5α-androstane;
3-oxo-4-aza-4-methyl-16β-methoxy-5α-androstane;
3-oxo-4-aza-4-methyl-16β-allyloxy-5α-androstane;
3-oxo-4-aza-4-methyl-16β-(n-propyloxy)-5α-androstane;
3-oxo-4-aza-4-methyl-16α-hydroxy-5α-androstane;
3-oxo-4-aza-4-methyl-16β-(phenoxy)-5α-androstane;
3-oxo-4-aza-7β-methyl-16β-(phenoxy)-5α-androst-1-ene;
3-oxo-4-aza-4-methyl-16α-methoxy-5α-androstane;
3-oxo-4-aza-4-methyl-16β-(4-chlorophenoxy)-5α-androstane;
3-oxo-4-aza-7β-methyl-16β-(4-chlorophenoxy)-5α-androst-1-ene;
3-oxo-4-aza-7β-methyl-16β-(4-cblorophenoxy)-5α-androstane;
3-oxo-4-aza-7β-methyl-16β-(3-chloro-4-methylphenoxy)-5α-androstane;
3-oxo-4-aza-7β-methyl-16β-(4-methylphenoxy)-5α-androstane;
3-oxo-4-aza-7β-methyl-16β-(4-methylphenoxy)-5α-androst-1-ene;
3-oxo-4-aza-7β-methyl-16β-[4-(1-pyrrolyl)phenoxy]-5α-androst-1-ene;
3-oxo-4-aza-4,7β-dimethyl-16β-hydroxy-5α-androstane;
3-oxo-4-aza-4,7β-dimethyl- 16β-methoxy-5α-androstane;
3-oxo-4-aza-4,7β-dimethyl-16β-allyloxy-5α-androstane;
3-oxo-4-aza-4,7β-dimethyl-16β-(3,3-dimethylallyloxy)-5α-androstane;
3-oxo-4-aza-4,7β-dimethyl-16β-(n-propyloxy)-5α-androstane;
3-oxo-4-aza-4,7β-dimethyl-16β-(iso-pentoxy)-5α-androstane;
3-oxo-4-aza-4,16α-dimethyl-16β-hydroxy-5α-androstane;
3-oxo-4-aza-4,7β-dimethyl-16β-ethyloxy-5α-androstane;
3-oxo-4-aza-4,7β-dimethyl-16β-benzyloxy-5α-androstane;
3-oxo-4-aza-4,7β-dimethyl-16α-hydroxy-5α-androstane;
3-oxo-4-aza-4,7β-dimethyl-16β-methylthio-5α-androstane;
3-oxo-4-aza-4,7β-dimethyl-16β-(n-propylthio)-5α-androstane;
3-oxo-4-aza-4,7β-dimethyl-16β-fluoro-5α-androstane;
3-oxo-4-aza-4,7β-dimethyl-16β-cyano-5α-androstane;
3-oxo-4-aza-4-methyl-16β-(1-hexyl)-5α-androstane;
3-oxo-4-aza-4,7β-dimethyl-16β-(n-propyl)-5α-androstane;
3-oxo-4-aza-4,7β-dimethyl-16β-benzyl-5α-androstane;
3-oxo-4-aza-4,7β-dimethyl-16β-(4-chlorobenzyl)-5α-androstane;

3-oxo-4-aza-4,16α-dimethyl-16β-methoxy-5α-androstane;
3-oxo-4-aza-4,7β-dimethyl-16β-(4-cyanophenoxy)-5α-androstane;
3-oxo-4-aza-4,7β-dimethyl-16β-(3-cyanophenoxy)-5α-androstane;
3-oxo-4-aza-4,7β-dimethyl-16β-(4-nitrophenoxy)-5α-androstane;
3-oxo-4-aza-4,7β-dimethyl-16β-(1-naphthyloxy)-5α-androstane;
3-oxo-4-aza-4,7β-dimethyl-16β-(3-chloro-4-methylphenoxy)-5α-androstane;
3-oxo-4-aza-4,7β-dimethyl-16β-(4-methylphenoxy)-5α-androstane;
3-oxo-4-aza-4,7β-dimethyl-16β-(tert-butyloxy)-5α-androstane;
3-oxo-4-aza-4,7β-dimethyl-16β-(3-methyl-1-butyloxy)-5α-androstane;
3-oxo-4-aza-4,7β-dimethyl-16α-(n-propyloxy)-5α-androstane;
3-oxo-4-aza-4,7β-dimethyl-16β-(4-trifluoromethylphenoxy)-5α-androstane;
3-oxo-4-aza-4,7β-dimethyl-16β-(4-trifluoromethoxyphenoxy)-5α-androstane;
3-oxo-4-aza-4,7β-dimethyl-16β-ethylthio-5α-androstane;
3-oxo-4-aza-4,7β-dimethyl-16β-ethylsulfonyl-5α-androstane;
3-oxo-4-aza-4,7β-dimethyl-16β-(4-methylsulfonylphenoxy)-5α-androstane;
3-oxo-4-aza-4,7β-dimethyl-16β-[4-(4-tolylsulfonylamino)phenoxy]-5α-androstane;
3-oxo-4-aza-4,7β-dimethyl-16β-(3-pyridyloxy)-5α-androstane;
3-oxo-4-aza-4,7β-dimethyl-16β-[(4-phenyl)phenoxy)-5α-androstane;
3-oxo-4-aza-4,7β-dimethyl-16β-(4-fluorophenoxy)-5α-androstane;
3-oxo-4-aza-4,7β-dimethyl-16β-(2-pyrazinyloxy)-5α-androstane;
3-oxo-4-aza-4,7β-dimethyl-16β-[4-(5-oxazolyl)phenoxy]-5α-androstane;
3-oxo-4-aza-4,7β-dimethyl-16β-(2-pyrimidinyloxy)-5α-androstane;
3-oxo-4-aza-4,7β-dimethyl-16β-[4-(1-pyrryl)phenoxy]-5α-androstane;
3-oxo-4-aza-4,7β-dimethyl-16β-(4-aminophenoxy)-5α-androstane;
3-oxo-4-aza-4,7β-dimethyl-16β-(4-acetylaminophenoxy)-5α-androstane;
3-oxo-4-aza-4,7β-dimethyl-16β-(4-benzoylanminophenoxy)-5α-androstane;
3-oxo-4-aza-4,7β-dimethyl-16β-(4-chlorophenoxy)-5α-androstane;
3-oxo-4-aza-4,7β-dimethyl-16β-(phenoxy)-5α-androstane;
3-oxo-4-aza-4,7β-dimethyl-16β-(2-chlorophenoxy)-5α-androstane;
3-oxo-4-aza-4,7β-dimethyl-16β-(3-chlorophenoxy)-5α-androstane;
3-oxo-4-aza-4,7β-dimethyl-16β-(4-chlorophenoxy)-5α-androst-1-ene;
3-oxo-4-aza-4,7β-dimethyl-16β-(4-chlorobenzylidene)-5α-androstane;
3-oxo-4-aza-4,7β-dimethyl-16-benzylidene-5α-androstane;
3-oxo-4-aza-4,7β-dimethyl-16-(4-methylbenzylidene)-5α-androstane;
3-oxo-4-aza-4,7β-dimethyl-16-(4-chlorobenzyl)-5α-androstane;
3-oxo-4-aza-4,7β-dimethyl-16-(4-methylbenzyl)-5α-androstane;
3-oxo-4-aza-4,7β-dimethyl-16-(3-pyridylmethyl)-5α-androstane;
3-oxo-4-aza-4,7β-dimethyl-16α-methanesulfonyl-5α-androstane;
3-oxo-4-aza-4,7β-dimethyl-16β-thiophenoxy-5α-androstane;
3-oxo-4-aza-4,7β-dimethyl-16β-(4-chlorothiophenoxy)-5α-androstane;
3-oxo-4-aza-4,7β-dimethyl-16β-(4-fluorothiophenoxy)-5α-androstane;
3-oxo-4-aza-4,7β-dimethyl-16β-(4-methylthiophenoxy)-5α-androstane;
3-oxo-4-aza-4,7β-dimethyl-16β-(4-methoxythiophenoxy)-5α-androstane;
3-oxo-4-aza-4,7β-dimethyl-16β-phenylsulfinyl-5α-androstane;
3-oxo-4-aza-4,7β-dimethyl-16β-phenylsulfonyl-5α-androstane;
3-oxo-4-aza-4,7β,16α-trimethyl-16β-(4-trifluoromethylphenoxy)-5α-androstane;
3-oxo-4-aza-4,7β,16α-trimethyl-16β-hydroxy-5α-androstane;
3-oxo-4-aza-4,7β,16α-trimethyl-16β-methoxy-5α-androstane;

pharmaceutically acceptable salts thereof, and analogs of the above-described compounds wherein the C1—C2 carbon-carbon bond is a double bond, and/or $R^1$ is —H, and/or $R^2$ is —H or methyl, where appropriate.

In another embodiment of compounds of Formula I are those further limited to those wherein the $C_1$–$C_2$ carbon-carbon bond is a single bond, $R^1$ is methyl, $R^2$ is methyl, $R^3$ is selected from unsubstituted or substituted aryloxy, and $R^4$ is hydrogen.

Some non-limiting examples of compounds of Formula I within this embodiment are:
3-oxo-4-aza-4,7β-dimethyl-16β-(4-cyanophenoxy)-5α-androstane;
3-oxo-4-aza-4,7β-dimethyl-16β-(3-cyanophenoxy)-5α-androstane;
3-oxo-4-aza-4,7β-dimethyl-16β-(4-nitrophenoxy)-5α-androstane;
3-oxo-4-aza-4,7β-dimethyl-16β-(1-naphthyloxy)-5α-androstane;
3-oxo-4-aza-4,7β-dimethyl-16β-(3-chloro-4-methylphenoxy)-5α-androstane;
3-oxo-4-aza-4,7β-dimethyl-16β-(4-methylphenoxy)-5α-androstane;
3-oxo-4-aza-4,7β-dimethyl-16β-(4-trifluoromethylphenoxy)-5α-androstane;
3-oxo-4-aza-4,7β-dimethyl-16β-(4-trifluoromethoxyphenoxy)-5α-androstane;
3-oxo-4-aza-4,7β-dimethyl-16β-(4-methylsulfonylphenoxy)-5α-androstane;
3-oxo-4-aza-4,7β-dimethyl-16β-[4-(4-tolylsulfonylamino)phenoxy]-5α-androstane;
3-oxo-4-aza-4,7β-dimethyl-16β-[(4-phenyl)phenoxy]-5α-androstane;
3-oxo-4-aza-4,7β-dimethyl-16β-(4-fluorophenoxy)-5α-androstane;
3-oxo-4-aza-4,7β-dimethyl-16β-[4-(5-oxazolyl)phenoxy]-5α-androstane;
3-oxo-4-aza-4,7β-dimethyl-16β-[4-(1-pyrryl)phenoxy]-5α-androstane;
3-oxo-4-aza-4,7β-dimethyl-16β-(4-aminophenoxy)-5α-androstane;
3-oxo-4-aza-4,7β-dimethyl-16β-(4-acetylaminophenoxy)-5α-androstane;

3-oxo-4-aza-4,7β-dimethyl-16β-(4-benzoylamino-phenoxy)-5α-androstane;

3-oxo-4-aza-4,7β-dimethyl-16β-(4-chlorophenoxy)-5α-androstane;

3-oxo-4-aza-4,7β-dimethyl-16β-(phenoxy)-5α-androstane;

3-oxo-4-aza-4,7,β-dimethyl-16β-(2-chlorophenoxy)-5α-androstane;

3-oxo-4-aza-4,7β-dimethyl-16β-(3-chlorophenoxy)-5α-androstane;

and the pharmaceutically acceptable salts thereof.

Particularly useful compounds of structural Formula I are 3-oxo-4-aza-4,7β-dimethyl-16β-(4-chlorophenoxy)-5α-androstane, 3-oxo-4-aza-4,7β-dimethyl-16β-(phenoxy)-5α-androstane, and 3-oxo-4-aza-7-methyl-16β-(4-methylphenoxy)-5α-androst-1-ene, or pharmaceutically acceptable salts thereof.

As used herein "alkyl" is intended to include both branched-and straight-chain saturated aliphatic hydrocarbon groups having the specified number of carbon atoms, e.g., methyl (Me), ethyl (Et), propyl, butyl, pentyl, hexyl, heptyl, octyl, nonyl, decyl, iso-propyl (i-Pr), iso-butyl (i-Bu), tert-butyl (t-Bu), sec-butyl (s-Bu), iso-pentyl, and the like. "Alkyloxy" (or "alkoxy") represents an alkyl group having the indicated number of carbon atoms attached through an oxygen bridge, e.g., methoxy, ethoxy, propyloxy, and the like. "Alkenyl" is intended to include hydrocarbon groups of either a straight or branched configuration with one or more carbon-carbon double bonds which may occur in any stable point along the chain, such as ethenyl, propenyl or allyl, butenyl, pentenyl, and the like. Included in this invention are all E, Z diastereomers.

The alkyl and alkenyl groups can be unsubstituted or substituted with one or more, and preferably 1-3, of:

i) halo; hydroxy; cyano; nitro; mono-, di- or trihalom-ethyl; oxo; hydroxysulfonyl; carboxy;

ii) hydroxy$C_{1-6}$alkyl; $C_{1-6}$alkyloxy; $C_{1-6}$ alkylthio; $C_{1-6}$alkylsulfonyl; $C_{1-6}$ alkyloxycarbonyl; in which the $C_{1-6}$ alkyl moiety can be further substituted with 1-3 of: halo; $C_{1-4}$ alkoxy; or trifluoromethyl;

iii) arylthio; aryl; aryloxy; arylsulfonyl; aryloxycarbonyl; in which the aryl moiety can be further substituted with 1-3 of: halo; $C_{1-4}$ alkyl; $C_{1-4}$ alkoxy; or trifluoromethyl;

iv) —C(O)NR$_b$R$_c$; —N(R$_b$)—C(O)—R$_c$; —NR$_b$R$_c$; where R$_b$ and R$_c$ are defined above; and halo is F, Cl, Br or I.

As used herein the term "aryl", i.e., $C_{6-10}$ aryl, is intended to mean phenyl or naphthyl, including 1-naphthyl and 2-naphthyl, either unsubstituted or substituted as described below.

The term "heteroaryl" as used herein, is intended to include a 5, 6 or 7 membered heteroaromatic radical containing at least one member selected from the group consisting of: one ring oxygen atom, one ring sulfur atom, 1–4 ring nitrogen atoms, or combinations thereof; in which the heteroaryl ring can also be fused with one benzo or heteroaromatic ring. This category includes the following either unsubstituted or substituted heteroaromatic rings (as described below): pyridyl, furyl, pyrryl, thienyl, isothiazolyl, imidazolyl, benzimidazolyl, tetrazolyl, pyrazinyl, pyrimidyl, quinolyl, quinazolinyl, isoquinolyl, benzofuryl, isobenzofuryl, benzothienyl, pyrazolyl, indolyl, isoindolyl, purinyl, carbazolyl, isoxazolyl, thiazolyl, isothiazolyl, oxazolyl, benzthiazolyl, and benzoxazolyl. The heteroaryl ring may be attached within structural Formula I by a heteroatom, e.g., N, or carbon atom in the ring, which results in the creation of a stable structure. The heteroaryl ring can also be fused to a benzo ring.

The one to three, and more usefully one to two substituents which can be on the $C_{6-10}$ aryl and heteroaryl groups named above are independently selected from:

v) halo; hydroxy; cyano; nitro; mono-, di- or trihalom-ethyl; mono-, di- or trihalomethoxy; $C_{2-6}$ alkenyl; $C_{3-6}$ cycloalkyl; formyl; hydrosulfonyl; carboxy; ureido;

vi) $C_{1-6}$ alkyl; hydroxy $C_{1-6}$ alkyl; $C_{1-6}$ alkyloxy; $C_{1-6}$ alkyloxy $C_{1-6}$alkyl; $C_{1-6}$ alkylcarbonyl; $C_{1-6}$ alkylsulfonyl; $C_{1-6}$ alkylthio; $C_{1-6}$ alkylsulfinyl; $C_{1-6}$ alkylsulfonamido; $C_{1-6}$ alkylarylsulfonamido; $C_{1-6}$ alkyloxycarbonyl; $C_{1-6}$ alkyloxycarbonyl $C_{1-6}$alkyl; R$_b$R$_c$N—C(O)—$C_{1-6}$alkyl; $C_{1-6}$ alkanoylamino $C_{1-6}$ alkyl; aroylamino $C_{1-6}$ alkyl; wherein the $C_{1-6}$ alkyl moiety can be substituted with 1–3 of: halo; $C_{1-4}$alkoxy; or trifluoromethyl;

vii) aryl; aryloxy; arylcarbonyl; arylthio; arylsulfonyl; arylsulfinyl; arylsulfonamido; aryloxycarbonyl; wherein the aryl moiety can be substituted with 1–3 of: halo; $C_{1-4}$alkyl; $C_{1-4}$alkoxy; or trifluoromethyl;

viii) —C(O)NR$_b$R$_c$; —O—C(O)—NR$_b$R$_c$; —N(R$_b$)—C(O)—R$_c$; —NR$_b$R$_c$; R$_b$—C(O)—N(R$_c$)—; where R$_b$ and R$_c$ are defined in (e) above; and —N(R$_b$)—C(O)—OR$_c$, wherein this instance R$_c$ is $C_{1-6}$alkyl or aryl; —N(R$_b$)—C(O) NR$_c$R$_d$, wherein R$_d$ is selected from H, $C_{1-6}$ alkyl, and aryl; in which said $C_{1-6}$alkyl and aryl can be substituted as described above in (e) for R$_b$ and R$_c$;

ix) a heterocyclic group, which is a 5, 6 or 7 membered ring, containing at least one member selected from the group consisting of: one ring oxygen atom, one ring sulfur atom, 1–4 ring nitrogen atoms, or combinations thereof; in which the heterocyclic ring can be aromatic, unsaturated, or saturated, and wherein the heterocyclic ring can be fused with a benzo ring, and wherein said heterocyclic ring can be substituted with one to three substituents, as defined above for v), vi), vii) and viii), excluding ix) a heterocyclic group.

The fused heteroaromatic ring systems include: purine, imidazoimidazole, imidazothiazole, pyridopyrimidine, pyridopyridazine, pyrimidopyrimidine, imidazopyridazine, pyrrolopyridine, imidazo-pyridine, and the like.

The "heterocyclic" group includes the fully unsaturated heteroaryl rings described above and also their respective dihydro, tetrahydro and hexahydro derivatives resulting in partially unsaturated and fully saturated versions of the ring systems. Examples include: dihydroimidazolyl, dihydrooxazolyl, dihydropyridyl, tetrahydrofuryl, dihydropyrryl, tetrahydrothienyl, dihydroisothiazolyl, 1,2-dihydrobenz-imidazolyl, 1,2-dihydrotetrazolyl, 1,2-dihydropyrazinyl, 1,2-dihydro-pyrimidyl, 1,2-dihydroquinolyl, 1,2,3,4-tetrahydroisoquinolyl, 1,2,3,4-tetrahydrobenzofuryl, 1,2,3,4-tetrahydroisobenzofuryl, 1,2,3,4-tetra-hydrobenzothienyl, 1,2,3,4-tetrahydropyrazolyl, 1,2,3,4-tetrahydro-indolyl, 1,2,3,4-tetrahydroisoindolyl, 1,2,3,4-tetrahydropurinyl, 1,2,3,4-tetrahydrocarbazolyl, 1,2,3,4-tetrahydroisoxazolyl, 1,2,3,4-tetrahydro-thiazolyl, 1,2,3,4-tetrahydrooxazolyl, 1,2,3,4-tetrahydrobenzthiazolyl, and 1,2,3,4-tetrahydrobenzoxazolyl. and the like.

The heterocyclic group can be substituted in the same ifashion as described above for heteroaryl.

Whenever the terms "alkyl", "alkenyl", "alkyloxy (or alkoxy)", "aryl" or "heteroaryl", or one of their prefix roots, appear in a name of a substituent in Formula I, (e.g., aralkoxyaryloxy) they shall have the same definitions as those described above for "alkyl", "alkenyl", "alkyloxy (or alkoxy)", "aryl" and "heteroaryl", respectively. Designated numbers of carbon atoms (e.g., $C_{1-10}$) shall refer independently to the number of carbon atoms in an alkyl or alkenyl moiety or to the alkyl or alkenyl portion of a larger substituent in which alkyl or alkenyl appears as its prefix root.

The term "pharmaceutically acceptable salt" is intended to include all acceptable salts such as acetate, lactobionate, benzenesulfonate, laurate, benzoate, malate, bicarbonate, maleate, bisulfate, mandelate, bitartrate, mesylate, borate, methylbromide, bromide, methylnitrate, calcium edetate, methylsulfate, camsylate, mucate, carbonate, napsylate, chloride, nitrate, clavulanate, N-methylglucamine, citrate, ammonium salt, dihydrochloride, oleate, edetate, oxalate, edisylate, pamoate (embonate), estolate, palmitate, esylate, pantothenate, fumarate, phosphate/diphosphate, gluceptate, polygalacturonate, gluconate, salicylate, glutamate, stearate, glycollylarsanilate, sulfate, hexylresorcinate, subacetate, hydrabamine, succinate, hydrobromide, tannate, hydrochloride, tartrate, hydroxynaphthoate, teoclate, iodide, tosylate, isothionate, triethiodide, lactate, panoate, valerate, and the like which can be used as a dosage form for modifying the solubility or hydrolysis characteristics or can be used in sustained release or pro-drug formulations.

The subject treated in the methods above is a mammal, preferably a human being, male or female, at risk of developing a disease where inhibiting bone loss may be beneficial, including: osteoporosis, osteopenia, Paget's disease, malignant hypercalcemia, periodontal disease, joint loosening and metastatic bone disease, as well as reducing the risk of fractures, both vertebral and nonvertebral. Alternatively the subject treated is a mammal, or preferably a human being, who has developed a disease where inhibiting bone loss may be beneficial, including: osteoporosis, osteopenia, Paget's disease, malignant hypercalcemia, periodontal disease, joint loosening and metastatic bone disease, as well as reducing the risk of fractures, both vertebral and nonvertebral.

A subject in need of the present invention may also be identified as possessing bone fractures.

The term "therapeutically effective amount" means the amount the compound of structural formula I that will elicit the biological or medical response of a tissue, system, animal or human that is being sought by the researcher, veterinarian, medical doctor or other clinician.

The term "composition" as used herein is intended to encompass a product comprising the specified ingredients in the specified amounts, as well as any product which results, directly or indirectly, from combination of the specified ingredients in the specified amounts.

By "pharmaceutically acceptable" it is meant the carrier, diluent or excipient must be compatible with the other ingredients of the formulation and not deleterious to the recipient thereof.

The terms "administration of" and or "administering a" compound should be understood to mean providing a compound of the invention or a prodrug of a compound of the invention to the individual in need of treatment.

The instant method of administering a compound of structural formula I is useful in the therapeutic or prophylactic treatment of disorders in calcium or phosphate metabolism and associated diseases. These diseases can be divided into two categories:

1. Abnormal (ectopic) depositions of calcium salts, mostly calcium phosphate, pathological hardening of tissues and bone malformations.
2. Conditions which can benefit from a reduction in bone resorption. A reduction in bone resorption should improve the balance between resorption and formation, reduce bone loss or result in bone augmentation. A reduction in bone resorption can aleviate the pain associated with osteolytic lesions and reduce the incidence and/or growth of those lesions.

These diseases include: osteoporosis (including estrogen defficiency, immobilization, glucocorticoid induced and senile), osteodystrophy, Paget's disease, myositis ossificans, Bechterew's disease, malignant hypercalcemia, metastatic bone disease, peridontal disease, cholelithiasis, nephrolithiasis, urolithiasis, urinary calculus, hardening of the arteries (sclerosis), arthritis, bursitis, neuritis and tetany, as well as reducing the risk of fractures, both vertebral and nonvertebral.

The administration of the compound of structural formula I in order to practice the present methods of therapy is carried out by administering an effective amount of the compound of structural formula I to the patient in need of such treatment or prophylaxis. The need for a prophylactic administration according to the methods of the present invention is determined via the use of well known risk factors. The effective amount of an individual compound is determined, in the final analysis, by the physician in charge of the case, but depends on factors such as the exact disease to be treated, the severity of the disease and other diseases or conditions from which the patient suffers, the chosen route of administration other drugs and treatments which the patient may concomitantly require, and other factors in the physician's judgment.

Generally, the daily dosage of the compound of structural formula I may be varied over a wide range from 0.01 to 1000 mg per adult human per day. Most preferably, dosages range from 0.1 to 50 mg/day. For oral administration, the compositions are preferably provided in the form of tablets containing 0.01 to 1000 mg, particularly 0.01, 0.05, 0.1, 0.5, 1.0, 2.5, 3.0, 5.0, 6.0, 10.0, 15.0, 25.0, and 50.0 milligrams of the active ingredient for the symptomatic adjustment of the dosage to the patient to be treated.

The dose may be administered in a single daily dose or the total daily dosage may be administered in divided doses of two, three or four times daily. Furthermore, when administered via intranasal routes, transdermal routes, by rectal suppositories, or through a continual intravenous solution, the dosage administration will, of course, be continuous rather than intermittent throughout the dosage regimen.

Formulations of the 5α-reductase inhibitor employed in the present method for medical use comprise the compound of structural formula I together with an acceptable carrier thereof and optionally other therapeutically active ingredients. The carrier must be pharmaceutically acceptable in the sense of being compatible with the other ingredients of the formulation and not deleterious to the recipient subject of the formulation.

The present invention, therefor further provides a pharmaceutical formulation comprising the compound of structural formula I together with a pharmaceutically acceptable carrier thereof.

The formulations include those suitable for oral, rectal, intravaginal, topical or parenteral (including subcutaneous, intramuscular and intravenous administration). Preferred are those suitable for oral administration.

The formulations may be presented in a unit dosage form and may be prepared by any of the methods known in the art of pharmacy. All methods include the step of bringing the active compound in association with a carrier which constitutes one or more ingredients. In general, the formulations are prepared by uniformly and intimately bringing the active compound in association with a liquid carrier, a waxy solid carrier or a finely divided solid carrier, and then, if needed, shaping the product into desired dosage form.

Formulations of the present invention suitable for oral administration may be presented as discrete units such as capsules, cachets, tablets or lozenges, each containing a predetermined amount of the active compound; as a powder or granules; or a suspension or solution in an aqueous liquid or non-aqueous. liquid, e.g., a syrup, an elixir, or an emulsion.

A tablet may be made by compression or molding, optionally with one or more accessory ingredients. Compressed tablets may be prepared by compressing in a suitable machine the active compound in a free flowing form, e.g., a powder or granules, optionally mixed with accessory ingredients, e.g., binders, lubricants, inert diluents, disintegrating agents or coloring agents. Molded tablets may be made by molding in a suitable machine a mixture of the active compound, preferably in powdered form, with a suitable carrier. Suitable binders include, without limitation, starch, gelatin, natural sugars such as glucose or beta-lactose, corn sweeteners, natural and synthetic gums such as acacia, tragacanth or sodium alginate, carboxymethyl-cellulose, polyethylene glycol, waxes and the like. Lubricants used in these dosage forms include, without limitation, sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

Oral liquid forms, such as syrups or suspensions in suitably flavored suspending or dispersing agents such as the synthetic and natural gums, for example, tragacanth, acacia, methyl cellulose and the like may be made by adding the active compound to the solution or suspension. Additional dispersing agents which may be employed include glycerin and the like.

Formulations for rectal administration may be presented as a suppository with a conventional carrier, i.e., a base that is nontoxic and nonirritating to mucous membranes, compatible with the compound of structural formula I, and is stable in storage and does not bind or interfere with the release of the compound of structural formula I. Suitable bases include: cocoa butter (theobroma oil), polyethylene glycols (such as carbowax and polyglycols), glycol-surfactant combinations, polyoxyl 40 stearate, polyoxyethylene sorbitan fatty acid esters (such as Tween, Myrj, and Arlacel), glycerinated gelatin, and hydrogenated vegetable oils. When glycerinated gelatin suppositories are used, a preservative such as methylparaben or propylparaben may be employed.

Topical preparations containing the active drug component can be admixed with a variety of carrier materials well known in the art, such as, e.g., alcohols, aloe vera gel, allantoin, glycerine, vitamin A and E oils, mineral oil, PPG2 myristyl propionate, and the like, to form, e.g., alcoholic solutions, topical cleansers, cleansing creams, skin gels, skin lotions, and shampoos in cream or gel formulations. See, e.g., EP 0 285 382.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinyl-pyrrolidone, pyran copolymer, polyhydroxypropylmethacrylamide-phenol, polyhydroxy-ethylaspartamidephenol, or polyethyleneoxide polylysine substituted with palmitoyl residues. Furthermore, the compounds of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

Formulations suitable for parenteral administration include formulations which comprise a sterile aqueous preparation of the active compound which is preferably isotonic with the blood of the recipient. Such formulations suitably comprise a solution or suspension of a compound that is isotonic with the blood of the recipient subject. Such formulations may contain distilled water, 5% dextrose in distilled water or saline and the active compound. Often it is useful to employ a pharmaceutically and pharmacologically acceptable acid addition salt of the active compound that has appropriate solubility for the solvents employed. Useful salts include the hydrochloride isothionate and methanesulfonate salts. Useful formulations also comprise concentrated solutions or solids comprising the active compound which on dilution with an appropriate solvent give a solution suitable for parenteral administration.

The compounds of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydro-pyrans, polycyanoacrylates and cross-linked or amphipathic block copolymers of hydrogels.

The pharmaceutical composition and method of the present invention may further comprise other therapeutically active compounds usually applied in the treatment of the above mentioned pathological conditions, for instance vitamin $D_2$ and $D_3$ and hydroxylated derivatives, e.g. 1α-hydroxy-vitamin $D_3$, 1α-hydroxy-vitamin $D_2$, 1α-25-dihydroxy-vitamin $D_3$, 1α-25-dihydroxy-vitamin $D_2$, dehydroepiandrosterone, calcitonin (human, porcine or salmon), mitramycin, sodium fluoride, estrogens, estrogen mimetics, including reloxafine and other compounds within the oxefine class, non-steroid antiinflammatory drugs, such as acetylsalicyclic acid, indomethacin, naprosyn, and timegadine, growth hormone secretagogues, growth hormone, growth hormone releasing hormone and insulin-like growth factor and bisphosphonates such as alendronate.

The composition and method of the present invention may further comprise a type 2 5α-reductase inhibitor or a dual 5α-reductase inhibitor. Preferred type 2 5α-reductase inhibitors for use in the present composition and method include: finasteride and epristeride. A preferred dual inhibitor is: 17β-N-(2,5-bis(trifluoromethyl))phenyl carbamoyl-4-aza-5α-androst-1-en-3-one.

One aspect of the present invention provides a method for inhibiting bone loss comprising administering to a mammal in need of treatment an effective amount of a compound of structural formula I.

Another aspect of the present invention provides the above-described method, and further comprises the coadministration of a bone antiresorptive agent and/or an anabolic agent and/or a 5α-reductase type 2 inhibitor. Bone antiresportive agents are those agents which are known in the art to inhibit the resorption of bone and include, for example, estrogen in which estrogen includes steroidal compounds having estrogenic activity such as, for example, 17β-estradiol, estrone, conjugated estrogen (PREMARIN®), equine estrogen, 17β-ethynyl estradiol, and the like.

Bisphosphonate compounds may also be employed in combination with the compound of structural formula I of the present invention include:

(a) 4-amino-1-hydroxybutylidene-1,1-bisphosphonic acid, (b) N-methyl-4-amino-hydroxybutylidene-1,1-bisphosphonic acid, (c) 4-(N,N-dimethylamino-1-hydroxybutylidene-1,1-bisphosphonic acid, (d) 3-amino-1-hydroxypropylidene-1,1-bisphosphonic acid, (e) 3-(N,N-dimethylamino)-1-hydroxypropylidene-1,1-bisphosphonic acid, (f) 1-hydroxy-3-(N-methyl-N-pentylamino)propylidene-1,1-bisphosphonic acid, (g) 1-hydroxy-2-(3-pyridyl)ethylidene-1,1-bisphosphonic acid, and (h) 4-(hydroxymethylene-1,1-bisphosphonic acid) piperidine, and their pharmaceutically acceptable salts. Especially preferred is alendronate, 4-amino-1-hydroxybutylidene-1,1-bisphosphonic acid monosodium salt, trihydrate. Methods for the preparation of bisphosphonic acids may be found in, e.g., U.S. Pat. No. 3,251,907; U.S. Pat. No. 3,422,137, U.S. Pat. No. 3,584,125; U.S. Pat. No. 3,940,436; U.S. Pat. No. 3,944,599; U.S. Pat. No. 3,962,432; U.S. Pat. No. 4,054,598; U.S. Pat. No. 4,267,108; U.S. Pat. No. 4,327,039; U.S. Pat. No. 4,407,761; U.S. Pat. No. 4,578,376; U.S. Pat. No. 4,621,077; U.S. Pat. No. 4,624,947; U.S. Pat. No. 4,746,654; U.S. Pat. No. 4,761,406; U.S. Pat. No. 4,922,077. In particular, methods for the preparation of 4-amino-1-hydroxybutylidene-1,1-bisphosphonic acid monosodium salt trihydrate may be found in U.S. Pat. No. 4,407,761 and U.S. Pat. No. 4,621,077.

Still further, antiestrogenic compounds such as raloxifene (see, e.g., U.S. Pat. No. 5,393,763) clomiphene, zuclomiphene, enclomiphene, nafoxidene, CI-680, CI-628, CN-55,945-27,Mer-25, U-11, 555A, U-100A, and salts thereof, and the like (see, e.g., U.S. Pat. Nos. 4,729,999 and 4,894,373) may be employed in combination with the compound of structural formula I in the methods and compositions of the present invention.

Bone anabolic agents are those agents which are known in the art to build bone by increasing the production of the bone protein matrix. Such anabolic agents include, for example, the various forms of parathyroid hormone (PTH) such as naturally occurring PTH (1–84), PTH (1–34), analogs thereof, growth hormone secretagogues, growth hormone, growth hormone releasing hormone and insulin-like growth factor and the like.

Representative growth hormone secretagogues are disclosed in U.S. Pat. No. 3,239,345; U.S. Pat. No. 4,036,979; U.S. Pat. No. 4,411,890; U.S. Pat. No. 5,206,235; U.S. Pat. No. 5,283,241; U.S. Pat. No. 5,284,841; U.S. Pat. No. 5,310,737; U.S. Pat. No. 5,317,017; U.S. Pat. No. 5,374,721; U.S. Pat. No. 5,430,144; U.S. Pat. No. 5,434,261; U.S. Pat. No. 5,438,136; U.S. Pat. No. 5,494,919; U.S. Pat. No. 5,494,920; U.S. Pat. No. 5,492,916; EPO Patent Pub. No. 0,144,230; EPO Patent Pub. No. 0,513,974; PCT Patent Pub. No. WO 94/07486; PCT Patent Pub. No. WO 94/08583; PCT Patent Pub. No. WO 94/11012; PCT Patent Pub. No. WO 94/13696; PCT Patent Pub. No. WO 94/19367; PCT Patent Pub. No. WO 95/03289; PCT Patent Pub. No. WO 95/03290; PCT Patent Pub. No. WO 95/09633; PCT Patent Pub. No. WO 95/11029; PCT Patent Pub. No. WO 95/12598; PCT Patent Pub. No. WO 95/13069; PCT Patent Pub. No. WO 95/14666; PCT Patent Pub. No. WO 95/16675; PCT Patent Pub. No. WO 95/16692; PCT Patent Pub. No. WO 95/17422; PCT Patent Pub. No. WO 95/17423; PCT Patent Pub. No. WO 95/34311; PCT Patent Pub. No. WO 96/02530; Science, 260, 1640–1643 (Jun. 11, 1993); Ann. Rep. Med. Chem., 28, 177–186 (1993); Bioor. Med. Chem. Ltrs., 4(22), 2709–2714 (1994); and Proc. Natl. Acad. Sci. USA 92, 7001–7005 (July 1995).

Representative growth hormone secretagogues are disclosed in U.S. Pat. No. 5,536,716 as spiro compounds of the following structural Formulas I and II:

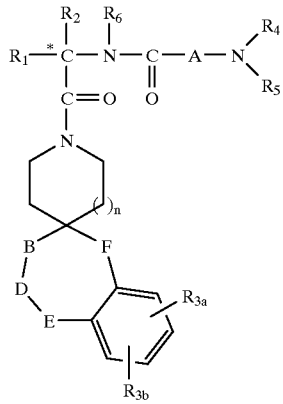

Formula I

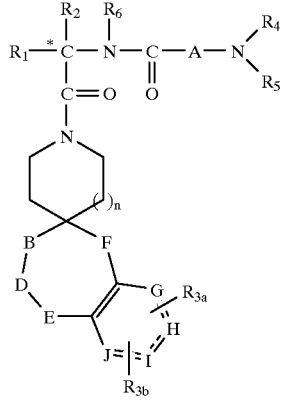

Formula II wherein the various substituents are as defined in U.S. Pat. No. 5,536,716.

Preferred growth hormone secretagogues for use in the present invention include:

N-[1(R)-[(1,2-Dihydro-1-methanesulfonylspiro[3H-indole-3,4'-piperidin]-1'-yl)carbonyl]-2-(phenylmethyloxy)ethyl]-2-amino-2-methylpropanamide; and N-[1(R)-[(1,2-Dihydro-1-methanesulfonylspiro[3H-indole-3,4'-piperidin]-1'-yl)carbonyl]-2-(phenylmethyl-oxy)ethyl]-2-amino-2-methylpropanamide methanesulfonate.

Especially preferred growth hormone secretagogues specifically include:

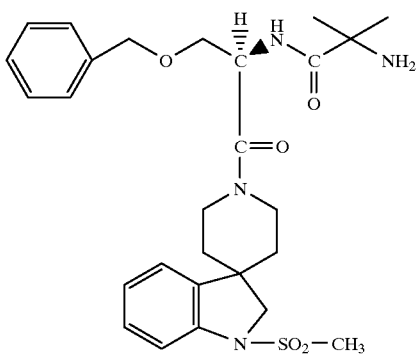

and pharmaceutically acceptable salts thereof; and

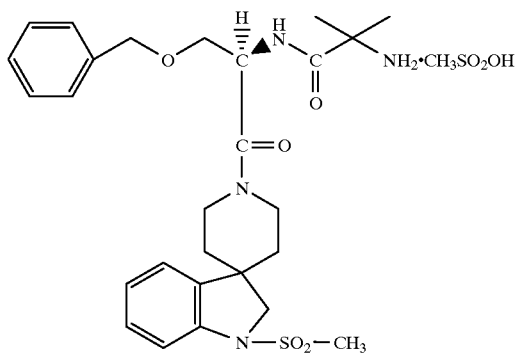

The preparation of growth hormone secretagogues is well known in the literature. Full descriptions of the preparation of the growth hormone secretagoues is found in e.g., U.S. Pat. No. 3,239,345; U.S. Pat. No. 4,036,979; U.S. Pat. No. 4,411,890; U.S. Pat. No. 5,206,235; U.S. Pat. No. 5,283,241; U.S. Pat. No. 5,284,841; U.S. Pat. No. 5,310,737; U.S. Pat. No. 5,317,017; U.S. Pat. No. 5,374,721; U.S. Pat. No. 5,430,144; U.S. Pat. No. 5,434,261; U.S. Pat. No. 5,438,136; U.S. Pat. No. 5,494,919; U.S. Pat. No. 5,494,920; U.S. Pat. No. 5,492,916; U.S. Pat. No. 5,536,716; EPO Patent Pub. No. 0,144,230; EPO Patent Pub. No. 0,513,974; PCT Patent Pub. No. WO 94/07486; PCT Patent Pub. No. WO 94/08583; PCT Patent Pub. No. WO 94/11012; PCT Patent Pub. No. WO 94/13696; PCT Patent Pub. No. WO 94/19367; PCT Patent Pub. No. WO 95/03289; PCT Patent Pub. No. WO 95/03290; PCT Patent Pub. No. WO 95/09633; PCT Patent Pub. No. WO 95/11029; PCT Patent Pub. No. WO 95/12598; PCT Patent Pub. No. WO 95/13069; PCT Patent Pub. No. WO 95/14666; PCT Patent Pub. No. WO 95/16675; PCT Patent Pub. No. WO 95/16692; PCT Patent Pub. No. WO 95/17422; PCT Patent Pub. No. WO 95/17423; PCT Patent Pub. No. WO 95/34311; PCT Patent Pub. No. WO 96/02530; *Science*, 260, 1640–1643 (Jun. 11, 1993); *Ann. Rep. Med. Chem.,* 28, 177–186 (1993); *Bioorg. Med. Chem. Ltrs.,* 4(22), 2709–2714 (1994); and *Proc. Natl. Acad. Sci. USA* 92, 7001–7005 (July 1995).

Daily dosage ranges for bone antiresorptive and anabolic agents and 5α-reductase type 2 inhibitors are those which are known in the art.

In particular, when a bisphosphonic acid is employed, dosages of 2.5 to 100 mg/day (measured as the free acid) are appropriate for treatment, more preferably 5 to 20 mg/day, especially about 10 mg/day. Prophylactically, doses of about 2.5 to about 10 mg/day and especially about 5 mg/day should be employed.

In particular, when a type 2 5α-reductase inhibitor or a dual 5α-reductase inhibitor is employed, dosages of 0.01 to 10 mg per adult human per day are appropriate for treatment, more preferably 1 to 5 mg/day especially preferred is about 5 mg/day.

The compounds of the methods of the present invention can be administered by a variety of routes including oral, rectal, transdermal, subcutaneous, intravenous, intramuscular, and intranasal, and such compounds are preferably formulated prior to administration. Therefore, another embodiment of the present invention is a pharmaceutical formulation comprising an effective amount of a compound of structural formula I or a pharmaceutically acceptable salt thereof, a bone antiresorptive or anabolic agent or a type 2 5α-reductase inhibitor or a dual 5α-reductase inhibitor, and a pharmaceutically acceptable carrier, diluent or excipient therefor.

In accordance with the method of the present invention, the individual components of the combination can be administered separately at different times during the course of therapy or concurrently in divided or single combination forms. The instant invention is therefore to be understood as embracing all such regimes of simultaneous or alternating treatment and the term "administering" is to be interpreted accordingly. It will be understood that the scope of combinations of the compounds of this invention with other agents useful for treating or preventing bone loss includes in principle any combination with any pharmaceutical composition useful for inhibiting bone loss or building new bone.

The compounds of structural formula I may be prepared as described in PCT publication WO 95/11254, and are available to one of ordinary skill in the art.

The 5α-reductase type 2 inhibitor finasteride that may employed this invention can be prepared as described in U.S. Pat. No. 4,760,071.

The following examples are not intended to be limitations on the scope of the instant invention in any way, and they should not be so construed. Furthermore, examples are not to be construed as forming the only methods and compositions that are considered as the invention. Those skilled in the art will readily understand that known variations of the conditions, processes, methods and compositions of the following preparative procedures can be used.

EXAMPLE 1

Effect of 3oxo-4-aza-4,7β-dimethyl-16β-(4-chlorophenoxy)-5α-androstane on bone mineral density in men Young men are entered into the study and are randomized to treatment with 5 mg/day 3-oxo-4-aza-4,7β-dimethyl-16β-(4-chlorophenoxy)-5α-androstane or placebo for 48 weeks. Lumbar spine bone mineral density, measured by dual energy X-ray absorptometry (DXA), and indices of bone metabolism, including Cross-Linked N-Telopeptides of Type 1 Collagen (NTX) and Bone-Specific Alkaline Phosphatase (BSAP) are measured at weeks 12, 24, 36 and 48.

EXAMPLE 2

Older men are enrolled in a 4-year, double-blind, placebo-controlled trial, and are randomly assigned to treatment with a compound of structural formula I or placebo. Bone density is measured at baseline, years 2, 3, and 4. Biochemical markers of bone are also measured at these time points.

EXAMPLE 3

Oral Composition

As a specific embodiment of an oral composition of a compound of this invention, 3 mg of 3-oxo-4-aza-4,7β- dimethyl-16β-(phenoxy)-5α-androstane is formulated with sufficient finely divided lactose to provide a total amount of 580 to 590 mg to fill a size 0 hard gelatin capsule.

EXAMPLE 4
Oral Composition

As a specific embodiment of an oral composition of a compound of this invention, 0.5 mg of 3-oxo-4-aza-7-methyl-16β-(4-methylphenoxy)-5α-androst-1-ene is formulated with sufficient finely divided lactose to provide a total amount of 580 to 590 mg to fill a size 0 hard gelatin capsule.

EXAMPLE 5
Oral Composition

As a specific embodiment of an oral composition of a compound of this invention, 2.5 mg of a compound of structural formula I is formulated with sufficient finely divided lactose to provide a total amount of 580 to 590 mg to fill a size 0 hard gelatin capsule.

EXAMPLE 6
Oral Composition

As a specific embodiment of an oral composition of a compound of this invention, 6 mg of 3-oxo-4-aza-4,7β-dimethyl-16β-(4-chlorophenoxy)-5α-androstane is formulated with sufficient finely divided lactose to provide a total amount of 580 to 590 mg to fill a size 0 hard gelatin capsule.

EXAMPLE 7
Transdermal Patch Formulation

| Ingredient | Amount |
| --- | --- |
| 3-oxo-4-aza-4,7β-dimethyl-16β-(phenoxy)-5α-androstane | 40 g |
| Silicone fluid | 45 g |
| Colloidal silicone dioxide | 2.5 g |

The silicone fluid and 3-oxo-4-aza-4,7β-dimethyl-16β-(phenoxy)-5α-androstane are mixed together and the colloidal silicone dioxide is added to increase viscosity. The material is then dosed into a subsequently heat sealed polymeric laminate comprised of the following: polyester release liner, skin contact adhesive composed of silicone or acrylic polymers, a control membrane which is a polyolefin (e.g. polyethylene, polyvinyl acetate or polyurethane), and an impermeable backing membrane made of a polyester multilaminate. The resulting laminated sheet is then cut into 10 cm² patches. For 100 Patches.

EXAMPLE 8
Suppository

| Ingredient | Amount |
| --- | --- |
| 3-oxo-4-aza-7-methyl-16β-(4-methylphenoxy)-5α-androst-1-ene | 25 g |
| Polyethylene glycol 1000 | 1481 g |
| Polyethylene glycol 4000 | 494 g |

The polyethylene glycol 1000 and polyethylene glycol 4000 are mixed and melted. The 3-oxo-4-aza-7-methyl-16β-(4-methylphenoxy)-5α-androst-1-ene is mixed into the molten mixture, poured into molds and allowed to cool. For 1000 suppositories.

EXAMPLE 9
Injectable solution

| Ingredient | Amount |
| --- | --- |
| compound of structural formula I | 5 g |
| Buffering agents | q.s. |
| Propylene glycol | 400 mg |
| Water for injection | 600 mL |

The compound of structural formula I and buffering agents are dissolved in the propylene glycol at about 50° C. The water for injection is then added with stirring and the resulting solution is filtered, filled into ampules, sealed and sterilized by autoclaving. For 1000 Ampules.

EXAMPLE 10
Injectable solution

| Ingredient | Amount |
| --- | --- |
| 3-oxo-4-aza-4,7β-dimethyl-16β-(4-chlorophenoxy)-5α-androstane | 5 g |
| Buffering agents | q.s. |
| Magnesium sulfate heptahydrate | 100 mg |
| Water for injection | 880 mL |

The 3-oxo-4-aza-4,7β-dimethyl-16β-(4-chlorophenoxy)-5α-androstane, magnesium sulfate heptahydrate and buffering agents are dissolved in the water for injection with stirring, and the resulting solution is filtered, filled into ampules, sealed and sterilized by autoclaving. For 1000 Ampules.

EXAMPLE 11
Oral Composition

As a specific embodiment of an oral composition of a compound of this invention, 5 mg of 3-oxo-4-aza-4,7β-dimethyl-16β-(phenoxy)-5α-androstane, 3 mg of finasteride (17β-(N-tert-butylcarbamoyl)-3-oxo-4-aza-5α-androst-1-en-3-one) and 2.5 mg of alendronate (4-amino-1-hydroxybutylidene-1,1-bisphosphonic acid monosodium salt trihydrate) is formulated with sufficient finely divided lactose to provide a total amount of 580 to 590 mg to fill a size 0 hard gelatin capsule.

EXAMPLE 12
Oral Composition

As a specific embodiment of an oral composition of a compound of this invention, 0.5 mg of 3-oxo-4-aza-7-methyl-16β-(4-methylphenoxy)-5α-androst-1-ene and 10.0 mg of alendronate (4-amino-1-hydroxybutylidene-1,1-bisphosphonic acid monosodium salt trihydrate) is formulated with sufficient finely divided lactose to provide a total amount of 580 to 590 mg to fill a size 0 hard gelatin capsule.

EXAMPLE 13
Oral Composition

As a specific embodiment of an oral composition of a compound of this invention, 2.5 mg of 3-oxo-4-aza-4,7β-dimethyl-16β-(4-chlorophenoxy)-5α-androstane and 5.0 mg of alendronate (4-amino-1-hydroxybutylidene-1,1-bisphosphonic acid monosodium salt trihydrate) are formulated with sufficient finely divided lactose to provide a total amount of 580 to 590 mg to fill a size 0 hard gelatin capsule.

EXAMPLE 14
Oral Composition

As a specific embodiment of an oral composition of a compound of this invention, 6 mg of a compound of structural formula I and 2.5 mg of alendronate (4-amino-1-hydroxybutylidene-1,1-bisphosphonic add monosodium salt trihydrate) is formulated with sufficient finely divided lactose to provide a total amount of 580 to 590 mg to fill a size 0 hard gelatin capsule.

EXAMPLE 15
Transdermal Patch Formulation

| Ingredient | Amount |
|---|---|
| alendronate | 50 g |
| 3-oxo-4-aza-7-methyl-16β-(4-methylphenoxy)-5α-androst-1-ene | 40 g |
| Silicone fluid | 45 g |
| Colloidal silicone dioxide | 2.5 g |

The silicone fluid alendronate and 3-oxo-4-aza-7-methyl-16β-(4-methylphenoxy)-5α-androst-1-ene are mixed together and the colloidal silicone dioxide is added to increase viscosity- The material is then dosed into a subsequently heat sealed polymeric laminate comprised of the following: polyester release liner, skin contact adhesive composed of silicone or acrylic polymers, a control membrane which is a polyolefin (e.g. polyethylene, polyvinyl acetate or polyurethane), and an impermeable backing membrane made of a polyester multilaminate. The resulting laminated sheet is then cut into 10 cm$^2$ patches. For 100 Patches.

EXAMPLE 16
Preparation of Human Prostatic and Scalp 5α-Reductases

Samples of human tissue were pulverized using a freezer mill and homogenized in 40 mM potassium phosphate, pH 6.5, 5 mM magnesium sulfate, 25 mM potassium chloride, 1 mM phenylmethyl-sulfonyl fluoride, 1 mM dithiothreitol (DTT) containing 0.25 M sucrose using a Potter-Elvehjem homogenizer. A crude nuclear pellet was prepared by centrifugation of the homogenate at 1,500×g for 15 min. The crude nuclear pellet was washed two times and resuspended in two volumes of buffer. Glycerol was added to the resuspended pellet to a final concentration of 20%. The enzyme suspension was frozen in aliquots at −80° C. The prostatic and scalp reductases were stable for at least 4 months when stored under these conditions.

EXAMPLE 17
5α-Reductase Assay

The reaction mixture for the type 1 5α-reductase contained 40 mM potassium phosphate, pH 6.5, 5 mM [7-$^3$H]-testosterone, 1 mM dithiothreitol and 500 μM NADPH in a final volume of 100 μL. The reaction mixture for the type 2 5α-reductase contained 40 mM sodium citrate, pH 5.5, 0.3 mM [7-$^3$H]-testosterone, 1 mM dithiothreitol and 500 μM NADPH in a final volume of 100 μL. Typically, the assay was initiated by the addition of 50–100 μg prostatic homogenate or 75–200 μg scalp homogenate and incubated at 37° C. After 10–50 min the reaction was quenched by extraction with 250 μL of a mixture of 70% cyclohexane: 30% ethyl acetate containing 10 μg each DHT and T. The aqueous and organic layers were separated by centrifugation at 14,000 rpm in an Eppendorf microfage. The organic layer was subjected to normal phase HPLC (10 cm Whatman Partisil 5 silica column equilibrated in 1 ml/min 70% cyclohexane: 30% ethyl acetate; retention times: DHT, 6.8–7.2 min; androstanediol, 7.6–8.0 min; T, 9.1–9.7 min). The HPLC system consisted of a Waters Model 680 Gradient System equipped with a Hitachi Model 655α Autosampler, Applied Biosystems Model 757 variable UV detector, and a Radiomatic Model A120 radioactivity analyzer. The conversion of T to DHT was monitored using the radioactivity flow detector by mixing the HPLC effluent with one volume of Flo Scint 1 (Radiomatic). Under the conditions described, the production of DHT was linear for at least 25 min. The only steroids observed with the human prostate and scalp preparations were T, DHT and androstanediol.

Inhibition Studies

Compounds were dissolved in 100% ethanol. The compound to be tested was pre-incubated with the enzyme (either 5α-reductase type 1 or 2) prior to initiation by addition of substrate testosterone. IC$_{50}$ values represent the concentration of inhibitor required to decrease enzyme conversion of testosterone to dihydrotestosterone by 50% of the control. IC$_{50}$ values were determined using a 6 point titration where the concentration of the inhibitor was varied from 0.1 to 1000 nM. Representative compounds of this invention were tested in the above described assay for 5α-reductase type 1 and type 2 inhibition.

A compound referred to herein as a 5α-reductase 2 inhibitor is a compound that shows inhibition of the 5α-reductase 2 isozyme in the above-described assay, having an IC$_{50}$ value of about or under 100 nM.

The compounds are tested in the above-described assay for 5α-reductase type 1 and type 2 inhibition, and were found to have IC$_{50}$ values under about 100 nM for inhibition of the type 1 isozyme. Compounds found to have IC$_{50}$ values of under about 50 nM for inhibition of the type 1 isozyme are called type 1 inhibitors. Compounds called "dual inhibitors" additionally had IC$_{50}$'s under about 200 nM for inhibition of the type 2 isozyme.

While the invention has been described and illustrated with reference to certain particular embodiments thereof, those skilled in the art will appreciate that various changes, modifications and substitutions can be made therein without departing from the spirit and scope of the invention. For example, effective dosages other than the particular dosages as set forth herein above may be applicable as a consequence of variations in the responsiveness of the mammal being treated for any of the indications for the compounds of the invention indicated above. Likewise, the specific pharmacological responses observed may vary according to and depending upon the particular active compound selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A method of inhibiting bone loss in a subject in need of such treatment comprising administration to the subject of an effective amount of a compound of structural formula I:

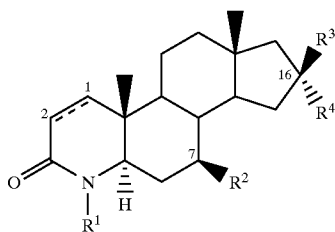

or a pharmaceutically acceptable salt or ester thereof wherein:

the C1—C2 carbon-carbon bond may be a single bond, or a double bond as indicated by the dashed line;

$R^1$ is selected from the group consisting of hydrogen and $C_{1-10}$ alkyl;

$R^2$ is selected from the group consisting of hydrogen and $C_{1-10}$ alkyl;

one of $R^3$ and $R^4$ is selected from the group consisting of hydrogen and methyl, and the other is selected from the group consisting of:
(a) amino;
(b) cyano;
(c) fluoro;
(d) methyl;
(e) OH;
(f) —C(O)$NR_bR_c$, where $R_b$ and $R_c$ are independently H, $C_{1-6}$ alkyl, aryl, or aryl$C_{1-6}$alkyl; wherein the alkyl moiety can be substituted with 1–3 of: halo; $C_{1-4}$alkoxy; or trifluoromethyl; and the aryl moiety can be substituted with 1–3 of: halo; $C_{1-4}$alkyl; $C_{1-4}$ alkoxy; or trifluoromethyl;
(g) $C_{1-10}$ alkyl—X—;
(h) $C_{2-10}$ alkenyl—X—;
wherein the $C_{1-10}$ alkyl in (g) and $C_{2-10}$ alkenyl in (h) can be unsubstituted or substituted with one to three of:
  i) halo; hydroxy; cyano; nitro; mono-, di- or trihalomethyl; oxo; hydroxysulfonyl; carboxy;
  ii) hydroxy$C_{1-6}$alkyl; $C_{1-6}$alkyloxy; $C_{1-6}$ alkylthio; $C_{1-6}$alkylsulfonyl; $C_{1-6}$ alkyloxycarbonyl; in which the $C_{1-6}$ alkyl moiety can be further substituted with 1–3 of: halo; $C_{1-4}$ alkoxy; or trifluoromethyl;
  iii) arylthio; aryl; aryloxy; arylsulfonyl; aryloxycarbonyl; in which the aryl moiety can be further substituted with 1–3 of: halo; $C_{1-4}$ alkyl; $C_{1-4}$ alkoxy; or trifluoromethyl;
  iv) —C(O)$NR_bR_c$; —N($R_b$)—C(O)—$R_c$; —$NR_bR_c$; where $R_b$ and $R_c$ are defined above;
(i) aryl—X—;
(j) heteroaryl—X—, wherein heteroaryl is a 5, 6 or 7 membered heteroaromatic ring containing at least one member selected from the group consisting of: one ring oxygen atom, one ring sulfur atom, 1–4 ring nitrogen atoms, or combinations thereof; in which the heteroaromatic ring can also be fused with one benzo or heteroaromatic ring;
wherein the aryl in (i) and heteroaryl in (j) can be unsubstituted or substituted with one to three of:
  v) halo; hydroxy; cyano; nitro; mono-, di- or trihalomethyl; mono-, di- or trihalomethoxy; $C_{2-6}$ alkenyl; $C_{3-6}$ cycloalkyl; formyl; hydrosulfonyl; carboxy; ureido;
  vi) $C_{1-6}$ alkyl; hydroxy $C_{1-6}$ alkyl; $C_{1-6}$ alkyloxy; $C_{1-6}$ alkyloxy $C_{1-6}$alkyl; $C_{1-6}$ alkylcarbonyl; $C_{1-6}$ alkylsulfonyl; $C_{1-6}$ alkylthio; $C_{1-6}$ alkylsulfinyl; $C_{1-6}$ alkylsulfonamido; $C_{1-6}$ alkylarylsulfonamido; $C_{1-6}$ alkyloxy-carbonyl; $C_{1-6}$ alkyloxycarbonyl $C_{1-6}$alkyl; $R_bR_cN$—C(O)—$C_{1-6}$alkyl; $C_{1-6}$ alkanoylamino $C_{1-6}$ alkyl; aroylamino $C_{1-6}$ alkyl; wherein the $C_{1-6}$ alkyl moiety can be substituted with 1–3 of: halo; $C_{1-4}$alkoxy; or trifluoromethyl;
  vii) aryl; aryloxy; arylcarbonyl; arylthio; arylsulfonyl; arylsulfinyl; arylsulfonamido; aryloxycarbonyl; wherein the aryl moiety can be substituted with 1–3 of: halo; $C_{1-4}$alkyl; $C_{1-4}$alkoxy; or trifluoromethyl;
  viii) —C(O)$NR_bR_c$; —O—C(O)—$NR_bR_c$; —N(Rb)—C(O)—$R_c$; —$NR_bR_c$; $R_b$—C(O)—N($R_c$)—; where $R_b$ and $R_c$ are defined in (f) above; and —N($R_b$)—C(O)—$OR_g$, wherein $R_g$ is $C_{1-6}$alkyl or aryl, in which the alkyl moiety can be substituted with 1–3 of: halo; $C_{1-4}$alkoxy; or trifluoromethyl, and the aryl moiety can be substituted with 1–3 of: halo; $C_{1-4}$alkyl; $C_{1-4}$ alkoxy, or trifluoromethyl; —N($R_b$)—C(O) $NR_cR_d$, wherein $R_d$ is selected from H, $C_{1-6}$ alkyl, and aryl; in which said $C_{1-6}$alkyl and aryl can be substituted as described above in (f) for $R_b$ and $R_c$;
  ix) a heterocyclic group, which is a 5, 6 or 7 membered ring, containing at least one member selected from the group consisting of: one ring oxygen atom, one ring sulfur atom, 1–4 ring nitrogen atoms, or combinations thereof; in which the heterocyclic ring can be aromatic, unsaturated, or saturated, wherein the heterocyclic ring can be fused with a benzo ring, and
wherein said heterocyclic ring can be substituted with one to three substituents, as defined above for v), vi), vii) and viii), excluding ix) a heterocyclic group; and
(k) $R^3$ and $R^4$ taken together can be carbonyl oxygen;
(l) $R^3$ and $R^4$ taken together can be =CH—$R_g$, wherein $R_g$ is defined in viii); and wherein:

X is selected from the group consisting of:
—O—; —S(O)$_n$—; —C(O)—; —CH($R_e$)—; —C(O)—O—*; —C(O)—N($R_e$)—*; —N($R_e$)—C(O)—O—*; —O—C(O)—N($R_e$)—*; —N($R_e$)C(O )—N($R_e$)—; —O—CH($R_e$)—*; —N($R_e$)—; wherein $R_e$ is H, $C_{1-3}$ alkyl, aryl, aryl- $C_{1-3}$ alkyl, or unsubstituted or substituted heteroaryl, as defined above in (j); wherein the asterisk (*) denotes the bond which is attached to the 16-position in Structure I; and n is zero, 1 or 2.

2. The method of claim 1 wherein the compound of structural formula I is selected from:

4-aza-4,7β-dimethyl-5α-androstane-3,16-dione;

4-aza-4-methyl-5α-androstan- 3, 16-dione;

3-oxo-4-aza-4-methyl-16β-hydroxy-5α-androstane;

3-oxo-4-aza-4-methyl-16β-(benzylaminocarbonyloxy)-5α-androstane;

3-oxo-4-aza-4-methyl-16β-benzoylamino-5α-androstane;

3-oxo-4-aza-4-methyl-16β-methoxy-5α-androstane;

3-oxo-4-aza-4-methyl-16β-allyloxy-5α-androstane;

3-oxo-4-aza-4-methyl-16β-(n-propyloxy)-5α-androstane;

3-oxo-4-aza-4-methyl-16α-hydroxy-5α-androstane;

3-oxo-4-aza-4-methyl-16β-(phenoxy)-5α-androstane;

3-oxo-4-aza-7β-methyl-16β-(phenoxy)-5α-androst-1-ene;

3-oxo-4-aza-4-methyl-16α-methoxy-5α-androstane;

3-oxo-4-aza-4-methyl-16β-(4-chlorophenoxy)-5α-androstane;

3-oxo-4-aza-7β-methyl-16β-(4-chlorophenoxy)-5α-androst-1-ene;

3-oxo-4-aza-7β-methyl-16β-(4-chlorophenoxy)-5α-androstane;

3-oxo-4-aza-7β-methyl-16β-(3-chloro-4-methylphenoxy)-5α-androstane;

3-oxo-4-aza-7β-methyl-16β-(4-methylphenoxy)-5α-androstane;

3-oxo-4-aza-7β-methyl-16β-(4-methylphenoxy)-5α-androst-1-ene;

3-oxo-4-aza-7β-methyl-16β-[4-(1-pyrrolyl)phenoxy]-5α-androst-1-ene;

3-oxo-4-aza-4,7β-dimethyl-16-hydroxy-5α-androstane;

3-oxo-4-aza-4,7β-dimethyl-16β-methoxy-5α-androstane;

3-oxo-4-aza-4,7β-dimethyl-16β-allyloxy-5α-androstane;

3-oxo-4-aza-4,7β-dimethyl-16β-(3,3-dimethylallyloxy)-5α-androstane;

3-oxo-4-aza-4,7β-dimethyl-16,β-(n-propyloxy)-5α-androstane;

3-oxo-4-aza-4,7β-dimethyl-16β-(iso-pentoxy)-5α-androstane;

3-oxo-4-aza-4,16α-dimethyl-16β-hydroxy-5α-androstane;

3-oxo-4-aza-4,7β-dimethyl-16β-ethyloxy-5α-androstane;

3-oxo-4-aza-4,7β-dimethyl-16β-benzyloxy-5α-androstane;

3-oxo-4-aza-4,7β-dimethyl-16α-hydroxy-5α-androstane;

3-oxo-4-aza-4,7β-dimethyl-16β-methylthio-5α-androstane;

3-oxo-4-aza-4,7β-dimethyl-16β-(n-propylthio)-5α-androstane;

3-oxo-4-aza-4,7β-dimethyl-16β-fluoro-5α-androstane;

3-oxo-4-aza-4,7β-dimethyl-16β-cyano-5α-androstane;

3-oxo-4-aza-4-methyl-16β-(1-hexyl)-5α-androstane;

3-oxo-4-aza-4,7β-dimethyl-16β-(n-propyl)-5α-androstane;

3-oxo-4-aza-4,7 β-dimethyl-16β-benzyl-5α-androstane;

3-oxo-4-aza-4,7β-dimethyl-16β-(4-chlorobenzyl)-5α-androstane;

3-oxo-4-aza-4,16α-dimethyl-16β-methoxy-5α-androstane;

3-oxo-4-aza-4,7β-dimethyl-16β-(4-cyanophenoxy)-5α-androstane;

3-oxo-4-aza-4,7β-dimethyl-16β-(3-cyanophenoxy)-5α-androstane;

3-oxo-4-aza-4,7β-dimethyl-16β-(4-nitrophenoxy)-5α-androstane;

3-oxo-4-aza-4,7β-dimethyl-16β-(1-naphthyloxy)-5α-androstane;

3-oxo-4-aza-4,7β-dimethyl-16β-(3-chloro-4-methylphenoxy)-5α-androstane;

3-oxo-4-aza-4,7β-dimethyl-16β-(4-methylphenoxy)-5α-androstane;

3-oxo-4-aza-4,7β-dimethyl-16β-(tert-butyloxy)-5α-androstane;

3-oxo-4-aza-4,7β-dimethyl-16β-(3-methyl-1-butyloxy)-5α-androstane;

3-oxo-4-aza-4,7β-dimethyl-16α-(n-propyloxy)-5α-androstane;

3-oxo-4-aza-4,7β-dimethyl-16β-(4-trifluoromethylphenoxy)-5α-androstane;

3-oxo-4-aza-4,7β-dimethyl-16β-(4-tiifluoromethoxyphenoxy)-5α-androstane;

3-oxo-4-aza-4,7β-dimethyl-16β-ethylthio-5α-androstane;

3-oxo-4-aza-4,7β-dimethyl-16β-ethylsulfonyl-5α-androstane;

3-oxo-4-aza-4,7β-dimethyl-16β-(4-methylsulfonyl-phenoxy)-5α-androstane;

3-oxo-4-aza-4,7β-dimethyl-16β-[4-(4-tolylsulfonyl-amino)phenoxy]-5α-androstane;

3-oxo-4-aza-4,7β-dimethyl-16β-(3-pyridyloxy)-5α-androstane;

3-oxo-4-aza-4,7β-dimethyl-16β-[(4-phenyl)phenoxy)-5α-androstane;

3-oxo-4-aza-4,7β-dimethyl-16β-(4-fluorophenoxy)-5α-androstane;

3-oxo-4-aza-4,7β-dimethyl-16β-(2-pyrazinyloxy)-5α-androstane;

3-oxo-4-aza-4,7β-dimethyl-16β-[4-(5-oxazolyl)phenoxy]-5α-androstane;

3-oxo-4-aza-4,7β-dimethyl-16β-(2-pyrinidinyloxy)-5α-androstane;

3-oxo-4-aza-4,7β-dimethyl-16β-[4-(1-pyrryl)phenoxy]-5α-androstane;

3-oxo-4-aza-4,7β-dimethyl-16β-(4-aminophenoxy)-5α-androstane;

3-oxo-4-aza-4,7β-dimethyl-16β-(4-acetylamino-phenoxy)-5α-androstane;

3-oxo-4-aza-4,7β-dimethyl-16β-(4-benzoylamino-phenoxy)-5α-androstane;

3-oxo-4-aza-4,7β-dimethyl-16β-(4-chlorophenoxy)-5α-androstane;

3-oxo-4-aza-4,7β-dimethyl-16β-(phenoxy)-5α-androstane;

3-oxo-4-aza-4,7β-dimethyl-16β-(2-chlorophenoxy)-5α-androstane;

3-oxo-4-aza-4,7β-dimethyl-16β-(3-chlorophenoxy)-5α-androstane;

3-oxo-4-aza-4,7β-dimethyl-16β-(4-chlorophenoxy)-5α-androst-1-ene;

3-oxo-4-aza-4,7β-dimethyl-16β-(4-chlorobenzylidene)-5α-androstane;

3-oxo-4-aza-4,7β-dimethyl-16-benzylidene-5α-androstane;

3-oxo-4-aza-4,7β-dimethyl-16-(4-methylbenzylidene)-5α-androstane;

3-oxo-4-aza-4,7β-dimethyl-16-(4-chlorobenzyl)-5α-androstane;

3-oxo-4-aza-4,7β-dimethyl-16-(4-methylbenzyl)-5α-androstane;

3-oxo-4-aza-4,7β-dimethyl-16-(3-pyridylmethyl)-5α-androstane;

3-oxo-4-aza-4,7β-dimethyl-16α-methanesulfonyl-5α-androstane;

3-oxo-4-aza-4,7β-dimethyl-16β-thiophenoxy-5α-androstane;

3-oxo-4-aza-4,7β-dimethyl-16β-(4-chlorothiophenoxy)-5α-androstane;

3-oxo-4-aza-4,7β-dimethyl-16β-(4-fluorothiophenoxy)-5α-androstane;

3-oxo-4-aza-4,7β-dimethyl-16β-(4-methylthiophenoxy)-5α-androstane;

3-oxo-4-aza-4,7β-dimethyl-16β-(4-methoxythiophenoxy)-5α-androstane;

3-oxo-4-aza-4,7β-dimethyl-16β-phenylsulfinyl-5α-androstane;

3-oxo-4-aza-4,7β-dimethyl-16β-phenylsulfonyl-5α-androstane;

3-oxo-4-aza-4,7β,16α-trimethyl-16β-(4-trifluoromethylphenoxy)-5α-androstane;

3-oxo-4-aza-4,7β,16α-trimethyl-16β-hydroxy-5α-androstane;

3-oxo-4-aza-4,7β,16α-trimethyl-16β-methoxy-5α-androstane;

3-oxo-4-aza-4,7β-dimethyl-16β-(4-cyanophenoxy)-5α-androstane;

3-oxo-4-aza-4,7β-dimethyl-16β-(3-cyanophenoxy)-5α-androstane;

3-oxo-4-aza-4,7β-dimethyl-16β-(4-nitrophenoxy)-5α-androstane;

3-oxo-4-aza-4,7β-dimethyl-16β-(1-naphthyloxy)-5α-androstane;

3-oxo-4-aza-4,7β-dimethyl-16β-(3-chloro-4-methylphenoxy)-5α-androstane;

3-oxo-4-aza-4,7β-dimethyl-16β-(4-methylphenoxy)-5α-androstane;

3-oxo-4-aza-4,7β-dimethyl-16β-(4-trifluoromethylphenoxy)-5α-androstane;

3-oxo-4-aza-4,7β-dimethyl-16β-(4-trifluoromethoxyphenoxy)-5α-androstane;

3-oxo-4-aza-4,7β-dimethyl-16β-(4-methylsulfonylphenoxy)-5α-androstane;

3-oxo-4-aza-4,7β-dimethyl-16β-[4-(4-tolylsulfonylamino)phenoxy]-5α-androstane;

3-oxo-4-aza-4,7β-dimethyl-16β-[(4-phenyl)phenoxy)-5α-androstane;

3-oxo-4-aza-4,7β-dimethyl-16β-(4-fluorophenoxy)-5α-androstane;

3-oxo-4-aza-4,7β-dimethyl-16β-[4-(5-oxazolyl)phenoxy]-5α-androstane;

3-oxo-4-aza-4,7β-dimethyl-16β-[4-(1-pyrryl)phenoxy]-5α-androstane;

3-oxo-4-aza-4,7β-dimethyl-16β-(4-aminophenoxy)-5α-androstane;

3-oxo-4-aza-4,7β-dimethyl-16β-(4-acetylaminophenoxy)-5α-androstane;

3-oxo-4-aza-4,7β-dimethyl-16β-(4-benzoylaminophenoxy)-5α-androstane;

3-oxo-4-aza-4,7β-dimethyl-16β-(4-chlorophenoxy)-5α-androstane;

3-oxo-4-aza-4,7β-dimethyl-16β-(phenoxy)-5α-androstane;

3-oxo-4-aza-4,7β-dimethyl-16β-(2-chlorophenoxy)-5α-androstane;

3-oxo-4-aza-4,7β-dimethyl-16β-(3-chlorophenoxy)-5α-androstane; and the pharmaceutically acceptable salts thereof.

3. The method of claim 1 wherein the compound of structural formula I selected from:

(a) 3-oxo-4-aza-4,7β-dimethyl-16β-(4-chlorophenoxy)-5α-androstane, (b) 3-oxo-4-aza-4,7β-dimethyl-16β-(phenoxy)-5α-androstane, and (c) 3-oxo-4-aza-7-methyl-16β-(4-methylphenoxy)-5α-androst-1-ene, or pharmaceutically acceptable salts thereof.

4. The method of claim 1 wherein the subject is a human.

5. The method of claim 1 wherein the compound of structural formula I is administered at a dose of 0.01 to 1000 mg per day.

6. The method of claim 5 wherein the compound of structural formula I is administered at a dose of 0.1 to 50 mg per day.

7. The method of inhibiting bone loss in a subject in need of such treatment according to claim 1 comprising administration of an effective amount of the compound of structural formula I and an effective amount of a bone anabolic agent or a bone antiresorptive agent or an inhibitor of 5α-reductase type 2 or a dual 5α-reductase inhibitor.

8. The method according to claim 7 wherein the bone anabolic agent is selected from a form of parathyroid hormone and a growth hormone secretagogue, growth hormone, growth hormone releasing hormone and insulin-like growth factor.

9. The method according to claim 8 wherein the growth hormone secretagogue is selected from:

(a) N-[1(R)-[( 1,2-Dihydro- 1-methanesulfonylspiro[3H-indole-3,4'-piperidin]-1'-yl)carbonyl]-2-(phenylmethyloxy)ethyl]-2-amino-2-methylpropanamide; and (b) N-[1(R)-[(1,2-Dihydro-1-methanesulfonylspiro[3H-indole-3,4'-piperidin]-1'-yl)carbonyl]-2-(phenylmethyloxy)ethyl]-2-amino-2-methylpropanamide methanesulfonate.

10. The method according to claim 7 wherein the bone antiresorptive agent is selected from:

(1) an estrogen, (2) a bisphosphonate compound, and (3) an antiestrogenic compound.

11. The method according to claim 10 wherein:

(1) the estrogen is selected from:
(a) 17β-estradiol,
(b) estrone,
(c) conjugated estrogen, equine estrogen, and
(d) 17β-ethynyl estradiol;

(2) the bisphosphonate compound is selected from:
(a) 4-amino-1-hydroxybutylidene-1,1-bisphosphonic acid,
(b) N-methyl-4-amino-hydroxybutylidene-1,1-bisphosphonic acid,
(c) 4-(N,N-dimethylamino-1-hydroxybutylidene-1,1-bisphosphonic acid,
(d) 3-amino-1-hydroxypropylidene-1,1-bisphosphonic acid,
(e) 3-(N,N-dimethylamino)-1-hydroxypropylidene-1,1-bisphosphonic acid,
(f) 1-hydroxy-3-(N-methyl-N-pentylamino)propylidene-1,1-bisphosphonic acid,
(g) 1-hydroxy-2-(3-pyridyl)ethylidene-1,1-bisphosphonic acid, and
(h) 4-(hydroxymethylene-1,1-bisphosphonic acid) piperidine; and (3) the antiestrogenic compound is selected from:
(a) raloxifene,
(b) clomiphene, (c) zuclomiphene,
(d) enclomiphene,
(e) nafoxidene,
(f) CI-680,
(g) CI-628,
(h) CN-55,945-27,
(i) Mer-25,
(j) U-11,
(k) 555A, and
(l) U-100A; and pharmaceutically acceptable salts thereof.

12. The method of inhibiting bone loss in a subject in need of such treatment according to claim 11 comprising administration of 0.1 to 50 mg/day of a compound of structural formula I selected from:
compound of structural formula I selected from:
(a) 3-oxo-4-aza-4,7β-dimethyl-16β-(4-chlorophenoxy)-5α-androstane,
(b) 3-oxo-4-aza-4,7β-dimethyl-16β-(phenoxy)-5α-androstane, and
(c) 3-oxo-4-aza-7-methyl-16β-(4-methylphenoxy)-5α-androst-1-ene, and pharmaceutically acceptable salts thereof;
together with 2.5 to 100 mg/day of 4-amino-1-hydroxybutylidene-1,1-bisphosphonic acid monosodium salt trihydrate.

13. The method according to claim 7 wherein:
the 5α-reductase type 2 inhibitor is selected from:
(a) finasteride, and
(b) epristeride; and
the dual 5α-reductase inhibitor is:
(a) 17β-N-(2,5-bis(trifluoromethyl))phenyl carbamoyl-4-aza-5α-androst-1-en-3-one.

14. A method of treating and preventing a disease involving bone resorption selected from: osteoporosis, osteopenia, Paget's disease, malignant hypercalcemia, periodontal disease, joint loosening and metastatic bone disease which comprises the administration to a subject in need thereof of an effective amount of a compound of structural formula I:

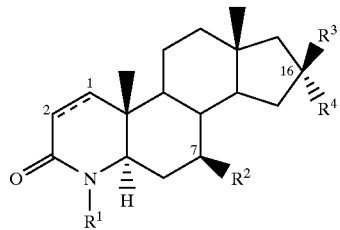

I or a pharmaceutically acceptable salt or ester thereof wherein:
the C1—C2 carbon-carbon bond may be a single bond, or a double bond as indicated by the dashed line;
$R^1$ is selected from the group consisting of hydrogen and $C_{1-10}$ alkyl;
$R^2$ is selected from the group consisting of hydrogen and $C_{1-10}$ alkyl;
one of $R^3$ and $R^4$ is selected from the group consisting of hydrogen and methyl, and the other is selected from the group consisting of:
(a) amino;
(b) cyano;
(c) fluoro;
(d) methyl;
(e) OH;
(f) —C(O)$NR_bR_c$, where $R_b$ and $R_c$ are independently H, $C_{1-6}$ alkyl, aryl, or aryl$C_{1-6}$alkyl; wherein the alkyl moiety can be substituted with 1–3 of: halo; $C_{1-4}$alkoxy; or trifluoromethyl; and the aryl moiety can be substituted with 1–3 of: halo; $C_{1-4}$alkyl; $C_{1-4}$ alkoxy; or trifluoromethyl;
(g) $C_{1-10}$ alkyl—X—;
(h) $C_{2-10}$ alkenyl—X—;
wherein the $C_{1-10}$ alkyl in (g) and $C_{2-10}$ alkenyl in (h) can be unsubstituted or substituted with one to three of:
i) halo; hydroxy; cyano; nitro; mono-, di- or trihalomethyl; oxo; hydroxysulfonyl; carboxy;
ii) hydroxy$C_{1-6}$alkyl; $C_{1-6}$alkyloxy; $C_{1-6}$ alkylthio; $C_{1-6}$alkylsulfonyl; $C_{1-6}$ alkyloxycarbonyl; in which the $C_{1-6}$ alkyl moiety can be firther substituted with 1–3 of: halo; $C_{1-4}$ alkoxy; or trifluoromethyl;
iii) arylthio; aryl; aryloxy; arylsulfonyl; aryloxycarbonyl; in which the aryl moiety can be further substituted with 1–3 of: halo; $C_{1-4}$ alkyl; $C_{1-4}$ alkoxy; or trifluoromethyl;
iv) —C(O)$NR_bR_c$; —N($R_b$)—C(O)—$R_c$; —$NR_bR_c$; where $R_b$ and $R_c$ are defined above;
(i) aryl—X—;
(j) heteroaryl—X—, wherein heteroaryl is a 5, 6 or 7 membered heteroaromatic ring containing at least one member selected from the group consisting of: one ring oxygen atom, one ring sulfur atom, 1–4 ring nitrogen atoms, or combinations thereof; in which the heteroaromatic ring can also be fused with one benzo or heteroaromatic ring;
wherein the aryl in (i) and heteroaryl in (j) can be unsubstituted or substituted with one to three of:
v) halo; hydroxy; cyano; nitro; mono-, di- or trihalomethyl; mono-, di- or trihalomethoxy; $C_{2-6}$ alkenyl; $C_{3-6}$ cycloalkyl; formyl; hydrosulfonyl; carboxy; ureido;
vi) $C_{1-6}$ alkyl; hydroxy $C_{1-6}$ alkyl; $C_{1-6}$ alkyloxy; $C_{1-6}$ alkyloxy $C_{1-6}$alkyl; $C_{1-6}$ alkylcarbonyl; $C_{1-6}$ alkylsulfonyl; $C_{1-6}$ alkylthio; $C_{1-6}$ alkylsulfinyl; $C_{1-6}$ alkylsulfonamido; $C_{1-6}$ alkylarylsulfonamido; $C_{1-6}$ alkyloxy-carbonyl; $C_{1-6}$ alkyloxycarbonyl $C_{1-6}$alkyl; $R_bR_cN$—C(O)—$C_{1-6}$alkyl; $C_{1-6}$ alkanoylamino $C_{1-6}$ alkyl; aroylamino $C_{1-6}$ alkyl; wherein the $C_{1-6}$ alkyl moiety can be substituted with 1–3 of: halo; $C_{1-4}$alkoxy; or trifluoromethyl;
vii) aryl; aryloxy; arylcarbonyl; arylthio; arylsulfonyl; arylsulfinyl; arylsulfonamido; aryloxycarbonyl; wherein the aryl moiety can be substituted with 1–3 of: halo; $C_{1-4}$alkyl; $C_{1-4}$alkoxy; or trifluoromethyl;
viii) —C(O)$NR_bR_c$; —O—C(O)—$NR_bR_c$; —N($R_b$)—C(O)—$R_c$; —$NR_bR_c$; $R_b$—C(O)—N($R_c$)—; where $R_b$ and $R_c$ are defined in (f) above; and —N($R_b$)—C(O)—$OR_g$, wherein $R_g$ is $C_{1-6}$alkyl or aryl, in which the alkyl moiety can be substituted with 1–3 of: halo; $C_{1-4}$alkoxy; or trifluoromethyl, and the aryl moiety can be substituted with 1–3 of: halo; $C_{1-4}$alkyl; $C_{1-4}$ alkoxy, or trifluoromethyl; —N($R_b$)—C(O) $NR_cR_d$, wherein $R_d$ is selected from H, $C_{1-6}$ alkyl, and aryl; in which said $C_{1-6}$alkyl and aryl can be substituted as described above in (f) for $R_b$ and $R_c$;
ix) a heterocyclic group, which is a 5, 6 or 7 membered ring, containing at least one member selected from the group consisting of: one ring oxygen atom, one ring sulfur atom, 1–4 ring nitrogen atoms, or combinations thereof; in which the heterocyclic ring can be aromatic, unsaturated, or saturated, wherein the heterocyclic ring can be fused with a benzo ring, and wherein said heterocyclic ring can be substituted with one to three substituents, as defined above for v), vi), vii) and viii), excluding ix) a heterocyclic group; and (k) $R^3$ and $R^4$ taken together can be carbonyl oxygen;

(l) $R^3$ and $R^4$ taken together can be $=CH-R_g$, wherein $R_g$ is defined in viii); and wherein:

X is selected from the group consisting of:
$-O-$; $-S(O)_n-$; $-C(O)-$; $-CH(R_e)-$; $-C(O)-O-^*$; $-C(O)-N(R_e)-^*$; $-N(R_e)-C(O)-O-^*$; $-O-C(O)-N(R_e)-^*$; $-N(R_e)C(O)-N(R_e)-$; $-O-CH(R_e)-^*$; $-N(R_e)-$; wherein $R_e$ is H, $C_{1-3}$ alkyl, aryl, aryl- $C_{1-3}$ alkyl, or unsubstituted or substituted heteroaryl, as defined above in (j); wherein the asterisk (*) denotes the bond which is attached to the 16-position in Structure I; and n is zero, 1 or 2.

15. The method of claim 14 wherein the compound of structural formula I is selected from:

4-aza-4,7β-dimethyl-5α-androstane-3,16-dione;

4-aza-4-methyl-5α-androstan- 3, 16-dione;

3-oxo-4-aza-4-methyl-16β-hydroxy-5α-androstane;

3-oxo-4-aza-4-methyl-16β-(benzylaminocarbonyloxy)-5α-androstane;

3-oxo-4-aza-4-methyl-16β-benzoylamino-5α-androstane;

3-oxo-4-aza-4-methyl-16β-methoxy-5α-androstane;

3-oxo-4-aza-4-methyl-16β-allyloxy-5α-androstane;

3-oxo-4-aza-4-methyl-16β-(n-propyloxy)-5α-androstane;

3-oxo-4-aza-4-methyl-16α-hydroxy-5α-androstane;

3-oxo-4-aza-4-methyl-16β-(phenoxy)-5α-androstane;

3-oxo-4-aza-7β-methyl-16β-(phenoxy)-5α-androst-1-ene;

3-oxo-4-aza-4-methyl-16α-methoxy-5α-androstane;

3-oxo-4-aza-4-methyl-16β-(4-chlorophenoxy)-5α-androstane;

3-oxo-4-aza-7β-methyl-16β-(4-chlorophenoxy)-5α-androst-1-ene;

3-oxo-4-aza-7β-methyl-16β-(4-chlorophenoxy)-5α-androstane;

3-oxo-4-aza-7β-methyl-16β-(3-chloro-4-methylphenoxy)-5α-androstane;

3-oxo-4-aza-7β-methyl-16β-(4-methylphenoxy)-5α-androstane;

3-oxo-4-aza-7β-methyl-16β-(4-methylphenoxy)-5α-androst-1-ene;

3-oxo-4-aza-7β-methyl-16β-[4-(1-pyrrolyl)phenoxy]-5α-androst-1-ene;

3-oxo-4-aza-4,7β-dimethyl-16β-hydroxy-5α-androstane;

3-oxo-4-aza-4,7β-dimethyl-16β-methoxy-5α-androstane;

3-oxo-4-aza-4,7β-dimethyl-16β-allyloxy-5α-androstane;

3-oxo-4-aza-4,7β-dimethyl-16β-(3,3-dimethylallyloxy)-5α-androstane;

3-oxo-4-aza-4,7β-dimethyl-16,β-(n-propyloxy)-5α-androstane;

3-oxo-4-aza-4,7β-dimethyl-16β-(iso-pentoxy)-5α-androstane;

3-oxo-4-aza-4,16α-dimethyl-16β-hydroxy-5α-androstane;

3-oxo-4-aza-4,7β-dimethyl-16β-ethyloxy-5α-androstane;

3-oxo-4-aza-4,7β-dimethyl-16β-benzyloxy-5α-androstane;

3-oxo-4-aza-4,7β-dimethyl-16α-hydroxy-5α-androstane;

3-oxo-4-aza-4,7β-dimethyl-16β-methylthio-5α-androstane;

3-oxo-4-aza-4,7β-dimethyl-16β-(n-propylthio)-5α-androstane;

3-oxo-4-aza-4,7β-dimethyl-16β-fluoro-5α-androstane;

3-oxo-4-aza-4,7β-dimethyl-16β-cyano-5α-androstane;

3-oxo-4-aza-4-methyl-16β-(1-hexyl)-5α-androstane;

3-oxo-4-aza-4,7β-dimethyl-16β-(n-propyl)-5α-androstane;

3-oxo-4-aza-4,7 β-dimethyl-16β-benzyl-5α-androstane;

3-oxo-4-aza-4,7β-dimethyl-16β-(4-chlorobenzyl)-5α-androstane;

3-oxo-4-aza-4,16α-dimethyl-16β-methoxy-5α-androstane;

3-oxo-4-aza-4,7β-dimethyl-16β-(4-cyanophenoxy)-5α-androstane;

3-oxo-4-aza-4,7β-dimethyl-16β-(3-cyanophenoxy)-5α-androstane;

3-oxo-4-aza-4,7β-dimethyl-16β-(4-nitrophenoxy)-5α-androstane;

3-oxo-4-aza-4,7β-dimethyl-16β-( 1-naphthyloxy)-5α-androstane;

3-oxo-4-aza-4,7β-dimethyl-16β-(3-chloro-4-methylphenoxy)-5α-androstane;

3-oxo-4-aza-4,7β-dimethyl-16β-(4-methylphenoxy)-5α-androstane;

3-oxo-4-aza-4,7β-dimethyl-16β-(tert-butyloxy)-5α-androstane;

3-oxo-4-aza-4,7β-dimethyl-16β-(3-methyl-1-butyloxy)-5α-androstane;

3-oxo-4-aza-4,7β-dimethyl-16α-(n-propyloxy)-5α-androstane;

3-oxo-4-aza-4,7β-dimethyl-16β-(4-trifluoromethyl-phenoxy)-5α-androstane;

3-oxo-4-aza-4,7β-dimethyl-16β-(4-tiifluoromethoxy-phenoxy)-5α-androstane;

3-oxo-4-aza-4,7β-dimethyl-16β-ethylthio-5α-androstane;

3-oxo-4-aza-4,7β-dimethyl-16β-ethylsulfonyl-5α-androstane;

3-oxo-4-aza-4,7β-dimethyl-16β-(4-methylsulfonyl-phenoxy)-5α-androstane;

3-oxo-4-aza-4,7β-dimethyl-16β-[4-(4-tolylsulfonyl-amino)phenoxy]-5α-androstane;

3-oxo-4-aza-4,7β-dimethyl-16β-(3-pyridyloxy)-5α-androstane;

3-oxo-4-aza-4,7β-dimethyl-16β-[(4-phenyl)phenoxy)-5α-androstane;

3-oxo-4-aza-4,7β-dimethyl-16β-(4-fluorophenoxy)-5α-androstane;

3-oxo-4-aza-4,7β-dimethyl-16β-(2-pyrazinyloxy)-5α-androstane;

3-oxo-4-aza-4,7β-dimethyl-16β-[4-(5-oxazolyl) phenoxy]-5α-androstane;

3-oxo-4-aza-4,7β-dimethyl-16β-(2-pyrinidinyloxy)-5α-androstane;

3-oxo-4-aza-4,7β-dimethyl-16β-[4-(1-pyrryl)phenoxy]-5α-androstane;

3-oxo-4-aza-4,7β-dimethyl-16β-(4-aminophenoxy)-5α-androstane;

3-oxo-4-aza-4,7β-dimethyl-16β-(4-acetylaminophenoxy)-5α-androstane;

3-oxo-4-aza-4,7β-dimethyl-16β-(4-benzoylaminophenoxy)-5α-androstane;

3-oxo-4-aza-4,7β-dimethyl-16β-(4-chlorophenoxy)-5α-androstane;

3-oxo-4-aza-4,7β-dimethyl-16β-(phenoxy)-5α-androstane;

3-oxo-4-aza-4,7β-dimethyl-16β-(2-chlorophenoxy)-5α-androstane;

3-oxo-4-aza-4,7β-dimethyl-16β-(3-chlorophenoxy)-5α-androstane;

3-oxo-4-aza-4,7β-dimethyl-16β-(4-chlorophenoxy)-5α-androst-1-ene;

3-oxo-4-aza-4,7β-dimethyl-16β-(4-chlorobenzylidene)-5α-androstane;

3-oxo-4-aza-4,7β-dimethyl-16-benzylidene-5α-androstane;

3-oxo-4-aza-4,7β-dimethyl-16-(4-methylbenzylidene)-5α-androstane;

3-oxo-4-aza-4,7β-dimethyl-16-(4-chlorobenzyl)-5α-androstane;

3-oxo-4-aza-4,7β-dimethyl-16-(4-methylbenzyl)-5α-androstane;

3-oxo-4-aza-4,7β-dimethyl-16-(3-pyridylmethyl)-5α-androstane;

3-oxo-4-aza-4,7β-dimethyl-16α-methanesulfonyl-5α-androstane;

3-oxo-4-aza-4,7β-dimethyl-16β-thiophenoxy-5α-androstane;

3-oxo-4-aza-4,7β-dimethyl-16β-(4-chlorothiophenoxy)-5α-androstane;

3-oxo-4-aza-4,7β-dimethyl-16β-(4-fluorothiophenoxy)-5α-androstane;

3-oxo-4-aza-4,7β-dimethyl-16β-(4-methylthiophenoxy)-5α-androstane;

3-oxo-4-aza-4,7β-dimethyl-16β-(4-methoxythiophenoxy)-5α-androstane;

3-oxo-4-aza-4,7β-dimethyl-16β-phenylsulfinyl-5α-androstane;

3-oxo-4-aza-4,7β-dimethyl-16β-phenylsulfonyl-5α-androstane;

3-oxo-4-aza-4,7β,16α-trimethyl-16β-(4-trifluoromethylphenoxy)-5α-androstane;

3-oxo-4-aza-4,7β,16α-trimethyl-16β-hydroxy-5α-androstane;

3-oxo-4-aza-4,7β,16α-trimethyl-16β-methoxy-5α-androstane;

3-oxo-4-aza-4,7β-dimethyl-16β-(4-cyanophenoxy)-5α-androstane;

3-oxo-4-aza-4,7β-dimethyl-16β-(3-cyanophenoxy)-5α-androstane;

3-oxo-4-aza-4,7β-dimethyl-16β-(4-nitrophenoxy)-5α-androstane;

3-oxo-4-aza-4,7β-dimethyl-16β-(1-naphthyloxy)-5α-androstane;

3-oxo-4-aza-4,7β-dimethyl-16β-(3-chloro-4-methylphenoxy)-5α-androstane;

3-oxo-4-aza-4,7β-dimethyl-16β-(4-methylphenoxy)-5α-androstane;

3-oxo-4-aza-4,7β-dimethyl-16β-(4-trifluoromethylphenoxy)-5α-androstane;

3-oxo-4-aza-4,7β-dimethyl-16β-(4-trifluoromethoxyphenoxy)-5α-androstane;

3-oxo-4-aza-4,7β-dimethyl-16β-(4-methylsulfonylphenoxy)-5α-androstane;

3-oxo-4-aza-4,7β-dimethyl-16β-[4-(4-tolylsulfonylamino)phenoxy]-5α-androstane;

3-oxo-4-aza-4,7β-dimethyl-16β-[(4-phenyl)phenoxy)-5α-androstane;

3-oxo-4-aza-4,7β-dimethyl-16β-(4-fluorophenoxy)-5α-androstane;

3-oxo-4-aza-4,7β-dimethyl-16β-[4-(5-oxazolyl)phenoxy]-5α-androstane;

3-oxo-4-aza-4,7β-dimethyl-16β-[4-(1-pyrryl)phenoxy]-5α-androstane;

3-oxo-4-aza-4,7β-dimethyl-16β-(4-aminophenoxy)-5α-androstane;

3-oxo-4-aza-4,7β-dimethyl-16β-(4-acetylaminophenoxy)-5α-androstane;

3-oxo-4-aza-4,7β-dimethyl-16β-(4-benzoylaminophenoxy)-5α-androstane;

3-oxo-4-aza-4,7β-dimethyl-16β-(4-chlorophenoxy)-5α-androstane;

3-oxo-4-aza-4,7β-dimethyl-16β-(phenoxy)-5α-androstane;

3-oxo-4-aza-4,7β-dimethyl-16β-(2-chlorophenoxy)-5α-androstane;

3-oxo-4-aza-4,7β-dimethyl-16β-(3-chlorophenoxy)-5α-androstane; and the pharmaceutically acceptable salts thereof.

16. The method of claim 14 wherein the compound of structural formula I is selected from:

(a) 3-oxo-4-aza-4,7β-dimethyl-16β-(4-chlorophenoxy)-5α-androstane, (b) 3-oxo-4-aza-4,7β-dimethyl-16β-(phenoxy)-5α-androstane, and (c) 3-oxo-4-aza-7-methyl-16β-(4-methylphenoxy)-5α-androst-1-ene, or pharmaceutically acceptable salts thereof.

17. The method of claim 14 wherein the compound of structural formula I is administered at a dose of 0.01 to 1000 mg per day.

18. The method of claim 14 wherein the compound of structural formula I is administered at a dose of 0.1 to 50 mg per day.

19. The method of treating and preventing a disease involving bone resorption selected from: osteoporosis, osteopenia, Paget's disease, malignant hypercalcemia, periodontal disease, joint loosening and metastatic bone disease in a subject in need thereof according to claim 14 comprising administration of an effective amount of the compound of structural formula I and an effective amount of a bone anabolic agent or a bone antiresorptive agent or a 5α-reductase type 2 inhibitor or a dual 5α-reductase inhibitor.

20. The method according to claim 19 wherein the bone anabolic agent is selected from a form of parathyroid hormone and a growth hormone secretagogue, growth hormone, growth hormone releasing hormone and insulin-like growth factor.

21. The method according to claim 20 wherein the growth hormone secretagogue is selected from:

(a) N-[1(R)-[( 1,2-Dihydro- 1-methanesulfonylspiro[3H-indole-3,4'-piperidin]-1'-yl)carbonyl]-2-(phenyl-methyloxy)ethyl]-2-amino-2-methylpropanamide; and (b) N-[1(R)-[( 1,2-Dihydro-1-methanesulfonylspiro[3H-indole-3,4'-piperidin]-1'-yl)carbonyl]-2-(phenyl-methyloxy)ethyl]-2-amino-2-methylpropanamide methanesulfonate.

22. The method according to claim 19 wherein the bone antiresorptive agent is selected from:

(1) an estrogen, (2) a bisphosphonate compound, and (3) an antiestrogenic compound.

23. The method according to claim 22 wherein:

(1) the estrogen is selected from:
 (a) 17β-estradiol,
 (b) estrone,
 (c) conjugated estrogen, equine estrogen, and
 (d) 17β-ethynyl estradiol;

(2) the bisphosphonate compound is selected from:
 (a) 4-amino-1-hydroxybutylidene-1,1-bisphosphonic acid,
 (b) N-methyl-4-amino-hydroxybutylidene-1,1-bisphosphonic acid,
 (c) 4-(N,N-dimethylamino-1-hydroxybutylidene-1,1-bisphosphonic acid,
 (d) 3-amino-1-hydroxypropylidene-1,1-bisphosphonic acid,
 (e) 3-(N,N-dimethylamino)-1-hydroxypropylidene-1,1-bisphosphonic acid,
 (f) 1-hydroxy-3-(N-methyl-N-pentylamino) propylidene-1,1-bisphosphonic acid,
 (g) 1-hydroxy-2-(3-pyridyl)ethylidene-1,1-bisphosphonic acid, and
 (h) 4-(hydroxymethylene-1,1-bisphosphonic acid) piperidine; and (3) the antiestrogenic compound is selected from:
 (a) raloxifene,
 (b) clomiphene,
 (c) zuclomiphene,
 (d) enclomiphene,
 (e) nafoxidene,
 (f) CI-680,
 (g) CI-628,
 (h) CN-55,945-27,
 (i) Mer-25,
 (j) U-11,
 (k) 555A, and
 (l) U-100A; and pharmaceutically acceptable salts thereof.

24. The method according to claim 23 comprising administration of 0.1 to 50 mg/day of the compound of structural formula I selected from:

(a) 3-oxo-4-aza-4,7β-dimethyl-16β-(4-chlorophenoxy)-5α-androstane, (b) 3-oxo-4-aza-4,7β-dimethyl-16β-(phenoxy)-5α-androstane, and (c) 3-oxo-4-aza-7-methyl-16β-(4-methylphenoxy)-5α-androst-1-ene, or a pharmaceutically acceptable salt thereof;

together with 2.5 to 100 mg/day of 4-amino-1-hydroxybutylidene-1,1-bisphosphonic acid monosodium salt trihydrate.

25. The method according to claim 19 wherein:

the 5α-reductase type 2 inhibitor is selected from:
(a) finasteride, and (b) epristeride; and the dual 5α-reductase inhibitor is:
(a) 17β-N-(2,5-bis(trifluoromethyl))phenyl carbamoyl-4-aza-5α-androst-1-en-3-one.

26. The method according to claim 14 wherein the bone resorption disease being prevented or treated is osteoporosis.

27. The method of claim 3 wherein the compound of structural formula I is 3-oxo-4-aza-7-methyl-16β-(4-methylphenoxy)-5α-androst-1-ene, or a pharmaceutically acceptable salt thereof.

28. A pharmaceutical composition comprising a pharmaceutically acceptable carrier, a therapeutically effective amount of a compound of structural formula I:

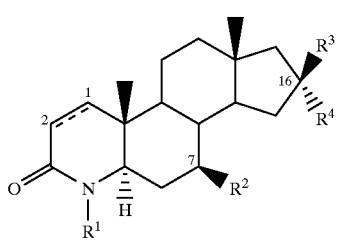

I or a pharmaceutically acceptable salt or ester thereof wherein:

the C1—C2 carbon-carbon bond may be a single bond, or a double bond as indicated by the dashed line;

$R^1$ is selected from the group consisting of hydrogen and $C_{1-10}$ alkyl;

$R^2$ is selected from the group consisting of hydrogen and $C_{1-10}$ alkyl;

one of $R^3$ and $R^4$ is selected from the group consisting of hydrogen and methyl, and the other is selected from the group consisting of:
(a) amino;
(b) cyano;
(c) fluoro;
(d) methyl;
(e) OH;
(f) —C(O)NR$_b$R$_c$, where R$_b$ and R$_c$ are independently H, $C_{1-6}$ alkyl, aryl, or aryl$C_{1-6}$alkyl; wherein the alkyl moiety can be substituted with 1–3 of: halo; $C_{1-4}$alkoxy; or trifluoromethyl; and the aryl moiety can be substituted with 1–3 of: halo; $C_{1-4}$alkyl; $C_{1-4}$ alkoxy; or trifluoromethyl;
(g) $C_{1-10}$ alkyl—X—;
(h) $C_{2-10}$ alkenyl—X—;

wherein the $C_{1-10}$ alkyl in (g) and $C_{2-10}$ alkenyl in (h) can be unsubstituted or substituted with one to three of:
 i) halo; hydroxy; cyano; nitro; mono-, di- or trihalomethyl; oxo; hydroxysulfonyl; carboxy;
 ii) hydroxy$C_{1-6}$alkyl; $C_{1-6}$alkyloxy; $C_{1-6}$ alkylthio; $C_{1-6}$alkylsulfonyl; $C_{1-6}$ alkyloxycarbonyl; in which the $C_{1-6}$ alkyl moiety can be firther substituted with 1–3 of: halo; $C_{1-4}$ alkoxy; or trifluoromethyl;
 iii) arylthio; aryl; aryloxy; arylsulfonyl; aryloxycarbonyl; in which the aryl moiety can be further substituted with 1–3 of: halo; $C_{1-4}$ alkyl; $C_{1-4}$ alkoxy; or trifluoromethyl;
 iv) —C(O)NR$_b$R$_c$; —N(R$_b$)—C(O)—R$_c$; —NR$_b$R$_c$; where R$_b$ and R$_c$ are defined above;

(i) aryl—X—;

(j) heteroaryl—X—, wherein heteroaryl is a 5, 6 or 7 membered heteroaromatic ring containing at least one member selected from the group consisting of: one ring oxygen atom, one ring sulfur atom, 1–4 ring nitrogen atoms, or combinations thereof; in which the heteroaromatic ring can also be fused with one benzo or heteroaromatic ring;

wherein the aryl in (i) and heteroaryl in (j) can be unsubstituted or substituted with one to three of:

v) halo; hydroxy; cyano; nitro; mono-, di- or trihalomethyl; mono-, di- or trihalomethoxy; $C_{2-6}$ alkenyl; $C_{3-6}$ cycloalkyl; formyl; hydrosulfonyl; carboxy; ureido;

vi) $C_{1-6}$ alkyl; hydroxy $C_{1-6}$ alkyl; $C_{1-6}$ alkyloxy; $C_{1-6}$ alkyloxy $C_{1-6}$alkyl; $C_{1-6}$ alkylcarbonyl; $C_{1-6}$ alkylsulfonyl; $C_{1-6}$ alkylthio; $C_{1-6}$ alkylsulfinyl; $C_{1-6}$ alkylsulfonamido; $C_{1-6}$ alkylarylsulfonamido; $C_{1-6}$ alkyloxy-carbonyl; $C_{1-6}$ alkyloxycarbonyl $C_{1-6}$alkyl; $R_b R_c N$—$C(O)$—$C_{1-6}$alkyl; $C_{1-6}$ alkanoylamino $C_{1-6}$ alkyl; aroylamino $C_{1-6}$ alkyl; wherein the $C_{1-6}$ alkyl moiety can be substituted with 1–3 of: halo; $C_{1-4}$alkoxy; or trifluoromethyl;

vii) aryl; aryloxy; arylcarbonyl; arylthio; arylsulfonyl; arylsulfinyl; arylsulfonamido; aryloxycarbonyl; wherein the aryl moiety can be substituted with 1–3 of: halo; $C_{1-4}$alkyl; $C_{1-4}$alkoxy; or trifluoromethyl;

viii) —$C(O)NR_b R_c$; —O—$C(O)$—$NR_b R_c$; —$N(R_b)$—$C(O)$—$R_c$; —$NR_b R_c$; $R_b$—$C(O)$—$N(R_c)$—; where $R_b$ and $R_c$ are defined in (f) above; and —$N(R_b)$—$C(O)$—$OR_g$, wherein $R_g$ is $C_{1-6}$alkyl or aryl, in which the alkyl moiety can be substituted with 1–3 of: halo; $C_{1-4}$alkoxy; or trifluoromethyl, and the aryl moiety can be substituted with 1–3 of: halo; $C_{1-4}$alkyl; $C_{1-4}$ alkoxy, or trifluoromethyl; —$N(R_b)$—$C(O)$ $NR_c R_d$, wherein $R_d$ is selected from H, $C_{1-6}$ alkyl, and aryl; in which said $C_{1-6}$alkyl and aryl can be substituted as described above in (f) for $R_b$ and $R_c$;

ix) a heterocyclic group, which is a 5, 6 or 7 membered ring, containing at least one member selected from the group consisting of: one ring oxygen atom, one ring sulfur atom, 1–4 ring nitrogen atoms, or combinations thereof; in which the heterocyclic ring can be aromatic, unsaturated, or saturated, wherein the heterocyclic ring can be fused with a benzo ring, and wherein said heterocyclic ring can be substituted with one to three substituents, as defined above for v), vi), vii) and viii), excluding ix) a heterocyclic group; and (k) $R^3$ and $R^4$ taken together can be carbonyl oxygen;

(l) $R^3$ and $R^4$ taken together can be =CH—$R_g$, wherein $R_g$ is defined in viii); and wherein:

X is selected from the group consisting of:
—O—; —S(O)$_n$—; —C(O)—; —CH($R_e$)—; —C(O)—O—$^*$; —C(O)—N($R_e$)—$^*$; —N($R_e$)—C(O)—O—$^*$; —O—C(O)—N($R_e$)—$^*$; —N($R_e$)C(O )—N($R_e$)—; —O—CH($R_e$)—$^*$; —N($R_e$)—; wherein $R_e$ is H, $C_{1-3}$ alkyl, aryl, aryl- $C_{1-3}$ alkyl, or unsubstituted or substituted heteroaryl, as defined above in (j); wherein the asterisk ($^*$) denotes the bond which is attached to the 16-position in Structure I; and n is zero, 1 or 2.

29. The pharmaceutical composition according to claim 28 comprising 0.1 to 50 mg of a compound of structural formula I selected from:

(a) 3-oxo-4-aza-4,7β-dimethyl-16β-(4-chlorophenoxy)-5α-androstane, (b) 3-oxo-4-aza-4,7β-dimethyl-16β-(phenoxy)-5α-androstane, and (c) 3-oxo-4-aza-7-methyl-16β-(4-methylphenoxy)-5α-androst-1-ene, or a pharmaceutically acceptable salt thereof; and 2.5 to 100 mg 4-amino-1-hydroxybutylidene-1,1-bisphosphonic acid.

* * * * *